(12) United States Patent
Hafenrichter et al.

(10) Patent No.: US 10,569,907 B2
(45) Date of Patent: Feb. 25, 2020

(54) APPARATUS FOR AUTOMATED MAINTENANCE OF AIRCRAFT STRUCTURAL ELEMENTS

(71) Applicant: The Boeing Company, Chicago, IL (US)

(72) Inventors: Joseph L. Hafenrichter, Seattle, WA (US); Gary E. Georgeson, Tacoma, WA (US)

(73) Assignee: The Boeing Company, Chicago, IL (US)

(*) Notice: Subject to any disclaimer, the term of this patent is extended or adjusted under 35 U.S.C. 154(b) by 458 days.

(21) Appl. No.: 15/244,927

(22) Filed: Aug. 23, 2016

(65) Prior Publication Data

US 2016/0368134 A1    Dec. 22, 2016

Related U.S. Application Data

(63) Continuation-in-part of application No. 14/036,464, filed on Sep. 25, 2013, now Pat. No. 9,481,082, which is a continuation-in-part of application No. 13/663,709, filed on Oct. 30, 2012, now Pat. No. 9,643,313, which is a continuation-in-part of application No. 12/657,424, filed on Jan. 19, 2010, now Pat. No. 8,347,746.

(51) Int. Cl.
*B64F 5/60*   (2017.01)
*B64F 5/40*   (2017.01)

(52) U.S. Cl.
CPC .............. *B64F 5/40* (2017.01); *Y10S 901/01* (2013.01)

(58) Field of Classification Search
CPC ....... B25J 5/00; B25J 9/02; B25J 11/005; B25J 11/008; Y10S 901/01
See application file for complete search history.

(56) References Cited

U.S. PATENT DOCUMENTS

| 3,575,043 | A | * | 4/1971 | Allen ................. G01N 29/2493 73/619 |
| 4,146,967 | A | | 4/1979 | Rohner et al. |
| 5,031,458 | A | | 7/1991 | Young et al. |
| 5,623,107 | A | | 4/1997 | Patterson, Sr. et al. |
| 5,698,787 | A | | 12/1997 | Parzuchowski et al. |
| 6,167,760 | B1 | | 1/2001 | Brunty et al. |

(Continued)

OTHER PUBLICATIONS

European Search Report dated May 31, 2011 for European Application No. 11151274.5 (European counterpart of U.S. Appl. No. 12/657,424, the ultimate parent application of the instant application).

(Continued)

*Primary Examiner* — Peter J Macchiarolo
*Assistant Examiner* — Alexander A Mercado
(74) *Attorney, Agent, or Firm* — Ostrager Chong Flaherty & Broitman P.C.

(57) ABSTRACT

Devices for maintaining crawler alignment on complex-shaped blades and for enabling the blade crawler to traverse over trailing edge protrusions. Using ball and socket bearings or air pads in place of alignment wheels, the crawler will be able to track along complex-geometry rotor blades, propellers and other airfoils. Using an oversized-diameter roller, a semi-flexible roller, or a dual-roller arrangement, the crawler will be able to traverse over trailing edge protrusions.

17 Claims, 19 Drawing Sheets

(56) References Cited

U.S. PATENT DOCUMENTS

| | | | |
|---|---|---|---|
| 6,220,099 B1 | 4/2001 | Marti et al. | |
| 6,378,387 B1 | 4/2002 | Froom | |
| 6,829,959 B2 | 12/2004 | Gifford et al. | |
| 7,083,383 B2 | 8/2006 | Loftus et al. | |
| 7,231,826 B2 | 6/2007 | Bossi et al. | |
| 7,240,556 B2 | 7/2007 | Georgeson et al. | |
| 7,315,609 B2 | 1/2008 | Safai et al. | |
| 7,337,673 B2 | 3/2008 | Kennedy et al. | |
| 7,562,593 B2 | 7/2009 | Engelbart et al. | |
| 7,626,383 B1 | 12/2009 | Sun et al. | |
| 7,640,811 B2 | 1/2010 | Kennedy et al. | |
| 7,716,989 B2 | 5/2010 | Kollgaard | |
| 8,281,442 B2 * | 10/2012 | Eggleston | B08B 1/02 15/21.1 |
| 8,483,356 B2 | 7/2013 | Bendahan | |
| 8,743,196 B2 | 6/2014 | Fritz et al. | |
| 9,334,066 B2 | 5/2016 | Tapia et al. | |
| 9,481,082 B1 * | 11/2016 | Hafenrichter | B25J 5/02 |
| 9,790,923 B2 * | 10/2017 | Krampe | F03D 17/00 |
| 2002/0036108 A1 | 3/2002 | Jeswine et al. | |
| 2003/0147493 A1 | 8/2003 | Bueno et al. | |
| 2005/0042102 A1 * | 2/2005 | Teichert | B08B 1/04 416/146 R |
| 2006/0043303 A1 | 3/2006 | Safai et al. | |
| 2006/0055396 A1 * | 3/2006 | Georgeson | G01N 29/265 324/202 |
| 2006/0055399 A1 * | 3/2006 | Georgeson | G01N 29/2481 324/232 |
| 2007/0096727 A1 | 5/2007 | Rempt et al. | |
| 2009/0038398 A1 | 2/2009 | Lavoie et al. | |
| 2009/0173573 A1 * | 7/2009 | Teichert | E04G 3/30 182/19 |
| 2010/0011864 A1 | 1/2010 | Hanan et al. | |
| 2010/0132137 A1 | 6/2010 | Eggleston et al. | |
| 2011/0127109 A1 * | 6/2011 | Teichert | F03D 80/50 182/19 |
| 2011/0178727 A1 | 7/2011 | Hafenrichter et al. | |
| 2012/0060611 A1 | 3/2012 | Thommen-Stamenkov et al. | |
| 2012/0153032 A1 | 6/2012 | Svanebjerg et al. | |
| 2013/0261876 A1 | 10/2013 | Froom et al. | |
| 2013/0289766 A1 | 10/2013 | Hafenrichter et al. | |
| 2013/0298682 A1 | 11/2013 | Motzer et al. | |
| 2013/0304251 A1 | 11/2013 | Garvey et al. | |
| 2014/0182479 A1 * | 7/2014 | Hafenrichter | B64F 5/60 105/30 |
| 2014/0305216 A1 * | 10/2014 | Hafenrichter | G01N 29/07 73/598 |
| 2014/0305217 A1 * | 10/2014 | Tapia | G01N 29/04 73/618 |
| 2015/0135459 A1 * | 5/2015 | Lee | B08B 7/04 15/246 |
| 2016/0334301 A1 * | 11/2016 | Hafenrichter | G01M 5/0075 |

OTHER PUBLICATIONS

MAUS Overview; http://www.boeing.com/defense-space/support/maintenance/commercial/maus.html; 4 pages.

European Search Report dated Feb. 24, 2016 for European Application No. 13182082.1 (European counterpart of U.S. Appl. No. 13/663,709, a parent application of the instant application).

\* cited by examiner

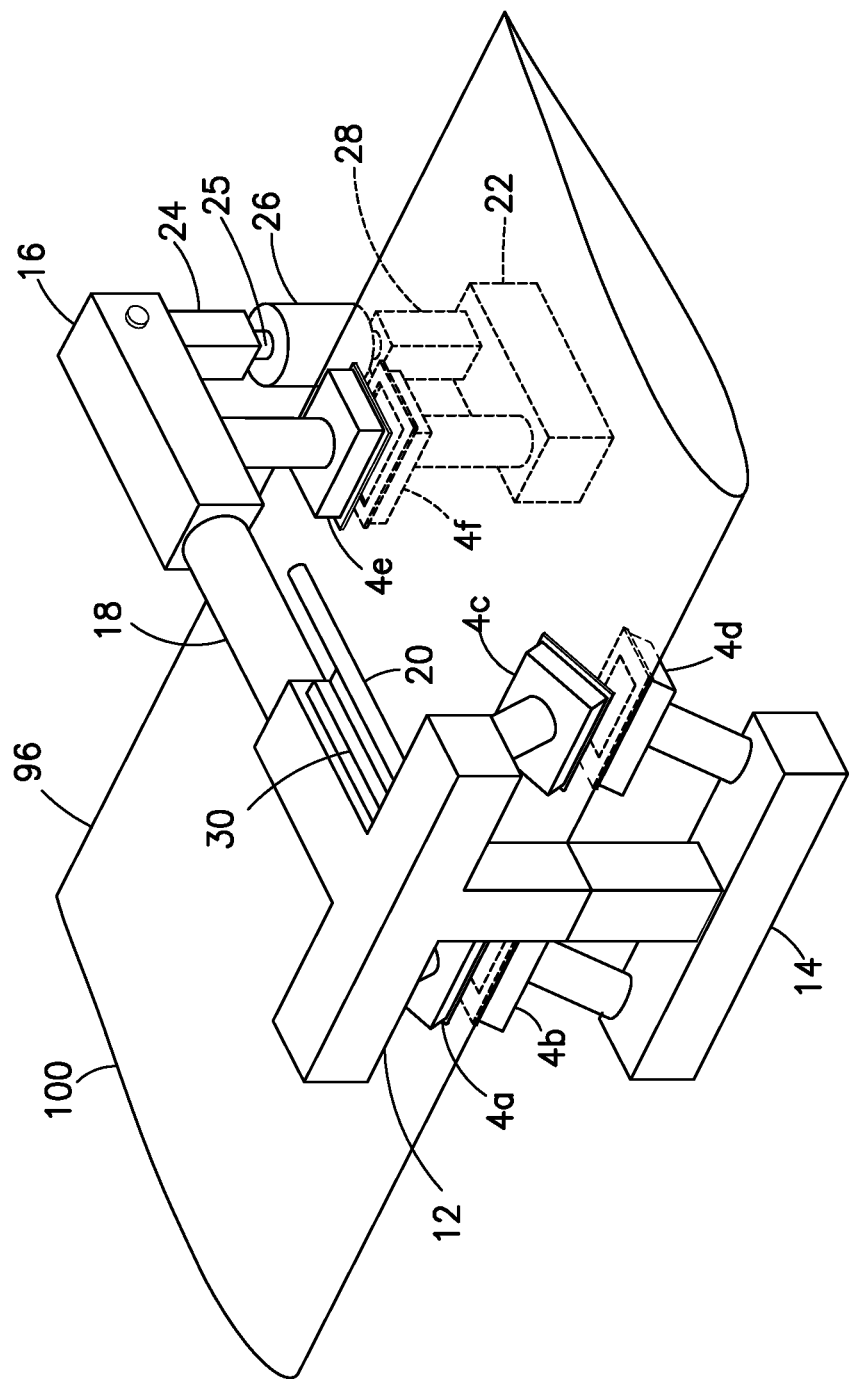

APPARATUS FOR AUTOMATED MAINTENANCE OF AIRCRAFT STRUCTURAL ELEMENTS

RELATED PATENT APPLICATIONS

This application is a continuation-in-part of and claims priority from U.S. patent application Ser. No. 14/036,464 filed on Sep. 25, 2013 and issued as U.S. Pat. No. 9,481,082 on Nov. 1, 2016, which application is a continuation-in-part of and claims priority from U.S. patent application Ser. No. 13/663,709 filed on Oct. 30, 2012, and issued as U.S. Pat. No. 9,643,313 on Oct. 31, 2013, which application is a continuation-in-part of and claims priority from U.S. patent application Ser. No. 12/657,424 filed on Jan. 19, 2010 and issued as U.S. Pat. No. 8,347,746 on Jan. 8, 2013. The disclosure of U.S. patent application Ser. No. 13/663,709 is incorporated by reference herein in its entirety.

BACKGROUND

The present disclosure relates generally to the field of automated maintenance (including nondestructive inspection) of aircraft structural elements such as airfoil-shaped bodies, and more particularly to an automated end effector-carrying apparatus that is coupled to and travels along an airfoil-shaped body having a relatively short chord length while performing a maintenance function. As used herein, the term "maintenance" includes, but is not limited to, operations such as nondestructive inspection (NDI), drilling, scarfing, grinding (e.g., to remove bonded or bolted components), fastening, appliqué application, ply mapping, depainting, cleaning and painting. Any one of a multiplicity of end effectors for performing a respective one of the foregoing maintenance functions can be attached to the apparatus. There are a number of types of blade components on aircraft that will benefit from maintenance automation, including rotorcraft blades, propeller blades, flaps, ailerons, trim tabs, slats, stabilators and stabilizers. As a whole, the automated apparatus reduces maintenance time, labor hours and human errors when robotic maintenance functions are performed on blade components.

U.S. patent application Ser. No. 13/663,709 discloses automated apparatus for performing maintenance functions on airfoil-shaped bodies having short chord lengths, without the necessity of removing the airfoil-shaped body from the aircraft. One such apparatus comprises a platform, an end effector carried by the platform, the end effector being selected from a group of interchangeable end effectors, means for mounting the end effector-carrying platform on an airfoil-shaped body, means for moving the end effector-carrying platform in a spanwise direction along the airfoil-shaped body, and means for moving the end effector in a chordwise direction relative to the airfoil-shaped body when the platform is stationary. In one implementation, the automated apparatus comprises a blade crawler which is movable in a spanwise direction and comprises a traveling element (e.g., a slider) that is linearly translatable in a chordwise direction when the spanwise-movable blade crawler is stationary. The selected end effector (mounted to the aforementioned slider) can be moved in a chordwise direction when the blade crawler is stationary.

The above-described blade crawler was designed to use the leading and trailing edge features of the blade to maintain its alignment with the blade. In practice, however, it can be difficult to maintain crawler alignment on complexly curved blades with twist, camber and sweep. A prototype blade crawler was developed having unidirectional rubber alignment wheels which tended to track along only straight paths along the blade. Although this crawler tracked well when traversing a constant-profile section of a blade, it tended to fall off the leading edge of the blade when encountering a section having a non-constant profile or complex curvature. The unidirectional rubber alignment wheels would continue along a straight path, even when the leading edge of the blade formed a curved path.

Another problem afflicting the aforementioned blade crawler prototype was an inability to traverse over trailing edge protrusions such as trim tabs, trim tab covers, and other irregularities. This inability to traverse trailing edge protrusions was mainly caused by a small-diameter follower wheel that is unable to climb over protrusions larger than its own radius.

An enhanced blade crawler capable of maintaining crawler alignment along a curved leading edge and/or traversing over trailing edge protrusions of a blade component would be advantageous.

SUMMARY

The subject matter disclosed herein is directed to devices for maintaining crawler alignment on complex-shaped blades as well as devices for enabling the blade crawler to traverse over trailing edge protrusions. The devices disclosed in detail below enable robust and automatic motion where the crawler tracks along complex curvature blades with twist, camber and sweep; and where the crawler traverses over trailing edge protrusions. With the ability to track along complex-geometry rotor blades, propellers and other airfoils, and with the ability to autonomously traverse over trailing edge protrusions without loss of functionality, a crawler equipped with the devices disclosed hereinafter can provide manufacturing and in-service automated NDI and repair functionality.

The foregoing is accomplished using five concepts that address the problems afflicting the aforementioned prototype crawler design: (1) Using ball and socket bearings or air pads in place of alignment wheels, the crawler will be able to track along complex-geometry rotor blades, propellers and other airfoils. (2) Using an oversized-diameter roller, a semi-flexible roller, or a dual-roller arrangement, the crawler will be able to traverse over trailing edge protrusions.

One aspect of the subject matter disclosed in detail below is an automated apparatus for moving an end effector over a surface of an airfoil-shaped body, comprising: a chassis configured to be mounted on an airfoil-shaped body, the chassis comprising forward and rearward assemblies which are linearly displaceable relative to each other along a first axis, the rearward assembly comprising an axle having a second axis perpendicular to the first axis; a drive roller rotatably mounted to the chassis; a first drive motor mounted to the chassis and arranged to drive rotation of the drive roller; a cross beam rotatably mounted to the axle of the rearward assembly of the chassis; a second drive motor arranged to drive rotation of the cross beam relative to the axle; and first and second rollers rotatably mounted to opposing ends of the cross beam for rotation about third and fourth axes respectively, the third and fourth axes being parallel to the second axis. In accordance with one embodiment, the apparatus further comprises a pivot gear mounted to an output shaft of the second drive motor and an axle reaction gear affixed to the axle, each of the pivot gear and the axle reaction gear comprising teeth that are interengaged.

The apparatus disclosed in the preceding paragraph may further comprise: a linear actuator for linearly displacing the rearward assembly relative to the forward assembly of the chassis, the linear actuator comprising a third drive motor; and a computer system configured to control the second and third drive motors in a protrusion climbing mode such that the cross beam rotates about the second axis and linearly displaces along the first axis concurrently.

Another aspect of the subject matter disclosed in detail below is an automated apparatus for moving an end effector over a surface of an airfoil-shaped body, comprising: a chassis configured to be mounted on an airfoil-shaped body, the chassis comprising forward and rearward assemblies which are linearly displaceable relative to each other along a first axis, the rearward assembly comprising a support member; a drive roller rotatably mounted to the chassis; a first drive motor mounted to the chassis and arranged to drive rotation of the drive roller; a second drive motor mounted to the support member and comprising an output shaft having a second axis perpendicular to the first axis; a cross beam mounted to the output shaft of the second drive motor; and first and second rollers rotatably mounted to opposing ends of the cross beam for rotation about third and fourth axes respectively, the third and fourth axes being parallel to the second axis.

A further aspect of the subject matter disclosed in detail below is an automated apparatus for moving an end effector over a surface of an airfoil-shaped body, comprising: a chassis configured to be mounted on an airfoil-shaped body, the chassis comprising forward and rearward assemblies which are linearly displaceable relative to each other along a first axis, the rearward assembly comprising an axle having a second axis perpendicular to the first axis; a drive roller rotatably mounted to the chassis; a first drive motor mounted to the chassis and arranged to drive rotation of the drive roller; a cross beam rotatably mounted to the axle of the rearward assembly of the chassis and not driven to rotate by a motor; first and second rollers rotatably mounted to opposing ends of the cross beam for rotation about third and fourth axes respectively, the third and fourth axes being parallel to the second axis; and a second drive motor for driving rotation of the first roller about the third axis.

In accordance with one embodiment, the apparatus described in the preceding paragraph further comprises: a drive pulley affixed to an output shaft of the second drive motor; a follower pulley rotatably coupled to the cross beam and fixedly coupled to the first roller; and a drive belt or chain that couples the follower pulley to the drive pulley. In accordance with another embodiment, the apparatus further comprises a third drive motor for driving rotation of the second roller about the fourth axis.

Yet another aspect of the subject matter disclosed in detail below is an automated apparatus for moving an end effector over a surface of an airfoil-shaped body, comprising: a chassis comprising forward and rearward assemblies, the rearward assembly being displaceable along an axis relative to the forward assembly; a drive roller coupled to the chassis for rolling in a direction which is transverse to the axis; a drive motor coupled to the driver roller and mounted to the chassis, the drive motor being capable of actuating rotation of the drive roller; and a follower roller coupled to the chassis for rolling in the transverse direction, wherein the follower roller comprises semi-flexible material such as soft elastomeric or semi-rigid foam.

Other aspects are disclosed and claimed below.

BRIEF DESCRIPTION OF THE DRAWINGS

FIG. 3 is an isometric view showing some components of a blade crawler having a plurality of air pads for maintaining alignment on the blade component. The end effector for performing a maintenance function and the means for scanning that end effector in a chordwise direction are not shown.

Reference will hereinafter be made to the drawings in which similar elements in different drawings bear the same reference numerals.

DETAILED DESCRIPTION

Figure 1:
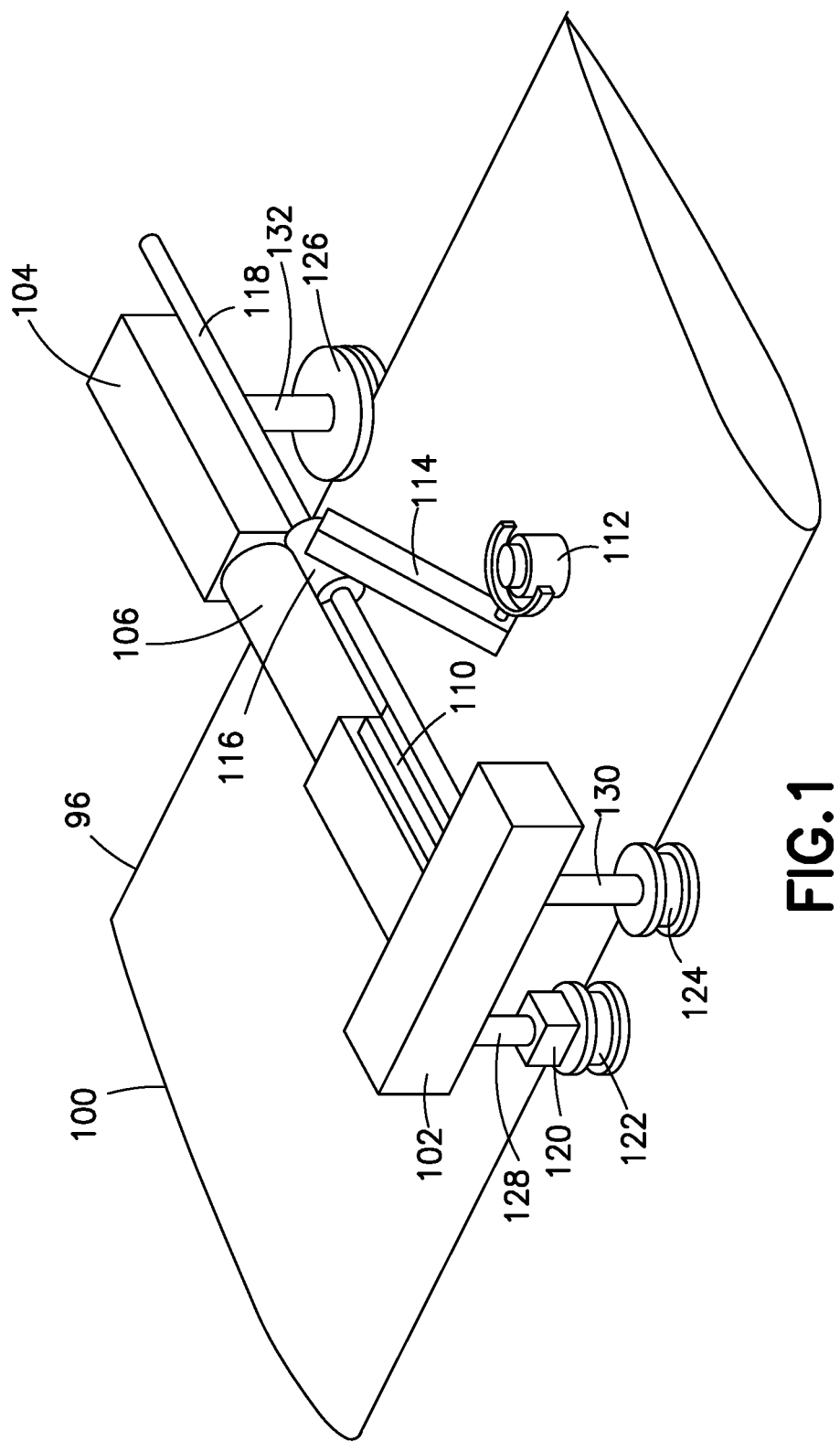
FIG. 1 is an isometric view of a blade crawler having a drive roller and a follower wheel and carrying a nondestructive inspection sensor, the crawler being mounted on an airfoil structure having a short chord length.

FIG. 1 shows one design for an autonomous, self-propelled, expandable and adjustable apparatus for inspecting in-service airfoil-shaped structures such as rotorcraft blades, aircraft propellers, smaller winglets, and narrow tail sections for structural damage by crawling along the length of the airfoil-shaped structure using the structure itself as the track, and employing scanning sensor mechanisms to acquire data representing the structural conditions found as the inspection apparatus moves across the surface.

As seen in FIG. 1, a scanning apparatus (hereinafter referred to as a "crawler") comprises a forward body part 102, a rearward body part 104, and an intercostal element 106 that interconnects the forward and rearward body parts to form a chassis. One of the forward and rearward body parts is displaceable along an axis of the intercostal element 106 to facilitate adjustment of the distance separating the forward and rearward body parts, while the other body part is fixed relative to the intercostal element 106. For example, the intercostal element 106 may comprise a circular cylindrical tube or rod having one end fixed to the forward body part 102, while a portion extending from the other end has the rearward body part 104 slidably mounted thereon in the manner of a telescoping sleeve, allowing the distance between the forward and rearward body parts to be adjusted to adapt to airfoil-shaped bodies having different chord lengths.

The forward body part 102 is positioned near a forward (i.e., leading) edge of the airfoil-shaped body 100 that is to be inspected (or subjected to some other maintenance procedure), and the rearward body part 104 is positioned near an opposing (i.e., trailing) edge of the airfoil-shaped body 100. Inspection of the airfoil-shaped body 100 is carried out, in part, by a face-sheet scanner 112 pivotally mounted on one end of an arm 114, the other end of the arm 114 in turn being pivotally mounted to a slider 116 coupled to and slidable on a guide rod 118. The guide rod 118 is integrally formed with a mounting plate 110 that is fastened to the forward body part 102. The face-sheet scanner 112 may comprise any one of a variety of NDI sensors to perform inspection of the airfoil-shaped body 100. To translate the face sheet scanner 112 chordwise across the airfoil-shaped body 100, a motor (not shown in FIG. 1) encased within the slider 116 interacts with the guide rod 118 via gears or friction wheels. Alternatively, the chordwise motion may be achieved by positioning the motor on the forward body part 102 and translating the slider 116 via a cable, drive belt, chain, or screw-drive in a well-known manner.

In accordance with one embodiment, the pivotally supported scanner 112 follows the curved surface of the airfoil-shaped body 100 when arm 114 exerts a normal force on the scanner 112. The normal force keeps the scanner 112 in intimate contact with the airfoil surface, thus enabling the NDI functionality of the scanner 112. The normal force exerted by the arm 114 can be generated by any conventional means, including the coupling of a spring, solenoid, pneumatic actuator or radial motion transducer (not shown in the drawings) between arm 114 and slider 116.

The forward body part 102 has a first rod 128 depending therefrom on which a control motor 120 is mounted. A drive roller 122 is mounted to an output shaft of the control motor 120. Rotation of drive roller 122 causes the crawler to travel in a spanwise direction provided that the drive roller 122 does not slip relative to the leading edge of the airfoil-shaped body 100. The forward body part 102 also has a second rod 130 depending therefrom on which a secondary follower wheel 124 is rotatably mounted. The secondary follower wheel 124 is displaced spanwise from the drive wheel 122 as shown. Additional means for maintaining crawler alignment with the airfoil-shaped body 100, such as a pair of rubber alignment wheels disposed near the leading edge, are not shown.

Still referring to FIG. 1, a shaft 132 depends from a rotary encoder (not shown) housed within the rearward body part 104 and carries an encoder wheel 126 on the free end thereof. The spanwise position of the crawler is measured by the rotary encoder, which encodes rotation of encoder wheel 126. The encoder wheel 126 rides on the trailing edge 96 as the crawler travels in the spanwise direction. The rotary encoder sends respective encoder pulses to an operations control center (e.g., via an encoder cable or a wireless connection) after each incremental movement of crawler in the spanwise direction. When the end effector is an NDI scanner, these encoder pulses are used by a control computer (not shown) and by ultrasonic pulser/receiver devices (not shown) to determine the spanwise coordinate of each scan plane in a well-known manner.

The drive roller 122, follower wheel 124 and encoder wheel 126 are held against, and in frictional engagement with, the leading and trailing edges, respectively, of the airfoil-shaped body 100 to be inspected. This is accomplished by application of a tensile force imparted to the forward and rearward body parts 102, 104 (to be discussed below). The front and rearward body parts in turn (in response to the tensile force applied between the front and rearward body parts) apply a compressive force on the blade component (via the drive roller 122, follower wheel 124 and encoder wheel 126) that holds the crawler on the airfoil-shaped body 100. The compressive force can be generated by a spring (not shown) which extends between the intercostal element 106 and the rearward body part 104.

In accordance with some implementations, various components of an end effector-carrying blade crawler communicate with a control computer (not shown in FIG. 1) located at an operations command center. In these instances, the control computer is connected to the blade crawler by an electrical cable. Alternatively, the control computer and the blade crawler could communicate wirelessly. The control computer may be programmed to control a cable management system (not shown). For example, motion control application software running on the control computer can control a cable motor of the cable management system. When the blade crawler is operated, one or more cables need to accompany the crawler down the length of the airfoil-shaped body, e.g., a helicopter blade. The motion control software running on the control computer synchronizes the movement of the cables with the movement of the blade crawler, extending or retracting the cables as appropriate. The computer system is programmed to control the cable motor in dependence on crawler spanwise-position information derived from pulses generated by a crawler position encoder. In addition, the control computer controls the crawler scan drive motor 120 in dependence on the pulses from the crawler position encoder.

When the crawler reaches a target spanwise position, the control computer shuts off the crawler scan drive motor 120 and then starts an end effector scan drive motor (not shown), e.g., a drive motor which moves slider 116 along the guide rod 118 seen in FIG. 1. The computer system is programmed to control the end effector scan drive motor in dependence on the end effector chordwise-position information derived from pulses generated by an end effector position encoder (not shown).

In cases where the end effector is a rotary tool (such as a scarfer, drill, deburrer or reamer), when the rotary tool reaches a target chordwise position, the control computer shuts off the end effector scan drive motor and then starts an end effector motor (not shown), e.g., a drive motor which drives rotation of the rotary tool. It should be appreciated that in cases where the end effector is emitting or ingesting a liquid or particles, the control computer will activate a pump. In cases where the end effector's elevational position is adjustable by operation of an actuator, such actuator may also be controlled by the computer.

Alternatively, in cases where a motion-producing device (such as a motor, solenoid, piston, etc.) is actuated to cause the crawler to grip the airfoil-shaped body, actuation of that motion-producing device may also be controlled by the control computer.

In accordance with the embodiments described above, the control computer is provided with information concerning the spanwise position of the crawler. This functionality can be provided by any one of a multiplicity of known positional tracking mechanisms.

The blade crawler shown in FIG. 1 can be adapted for use in the automation of various maintenance functions, including but not limited to nondestructive inspection, drilling, grinding, fastening, appliqué application, scarfing, ply mapping, depainting, cleaning and painting. There are a number of types of blade components on aircraft that will benefit from maintenance automation, including rotorcraft blades, propeller blades, flaps, ailerons, trim tabs, slats, stabilators and stabilizers.

The alignment and movement of automated blade crawlers of the type shown in FIG. 1 can be enhanced by the addition of devices able to track complex-geometry rotor blades, propellers and other airfoil-shaped bodies. Two embodiments of devices for maintaining crawler alignment during spanwise motion of the crawler will now be described with reference to FIGS. 2 and 3.

Figure 2:
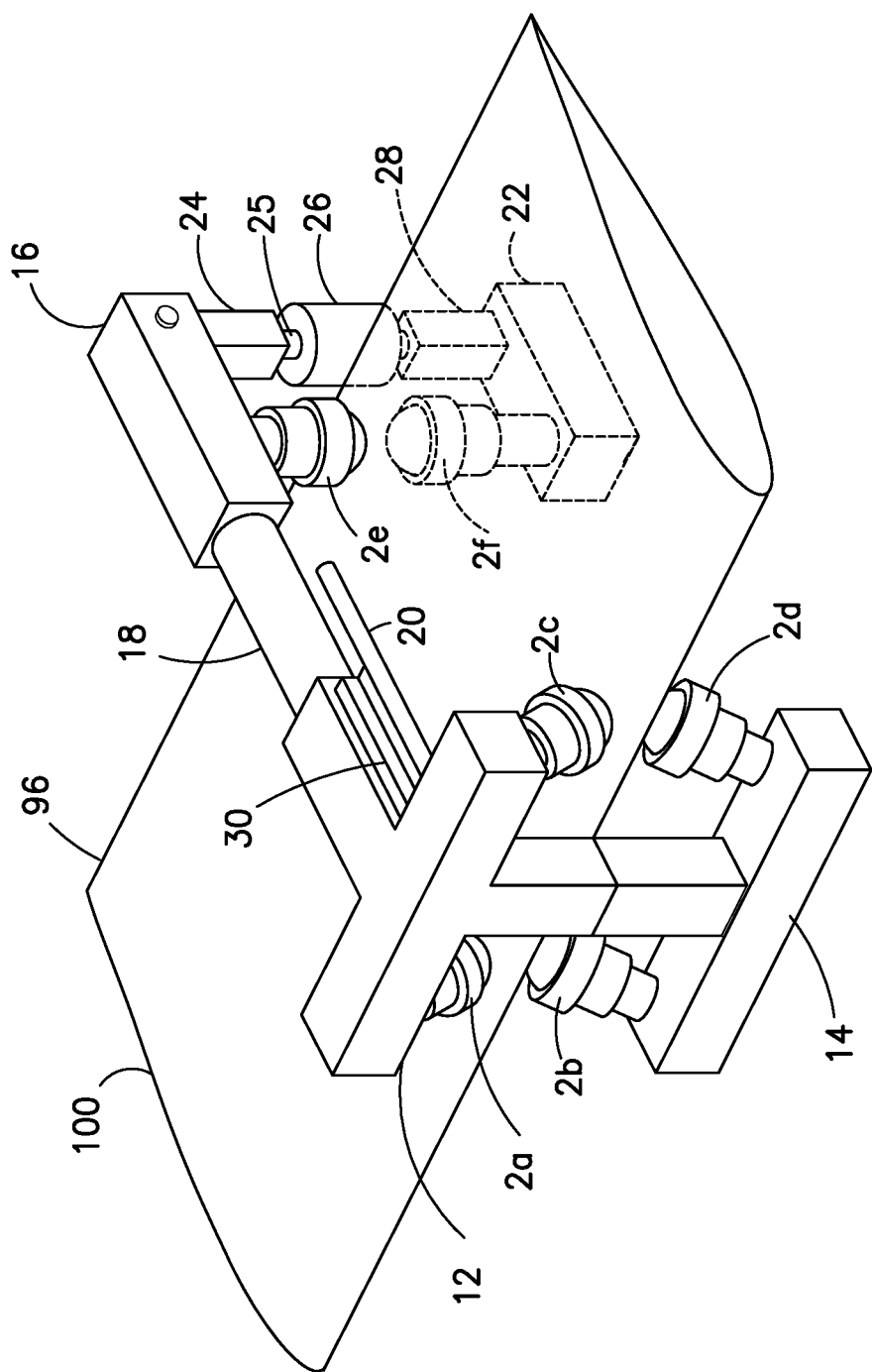
FIG. 2 is an isometric view showing some components of a blade crawler having a plurality of ball and socket bearings for maintaining alignment on the blade component. The end effector for performing a maintenance function and the means for scanning that end effector in a chordwise direction are not shown to avoid clutter in the drawing.

FIG. 2 shows portions of a blade crawler having a plurality of ball and socket bearings $2a$ through $2f$ for maintaining alignment on an airfoil-shaped body 100. The chassis of the blade crawler comprises an upper forward body part 12, an upper rearward body part 16, and an intercostal element 18 that interconnects the upper forward and rearward body parts. One of the upper forward and rearward body parts is displaceable along an axis of the intercostal element 18 to facilitate adjustment of the distance separating the upper forward and rearward body parts, while the other body part is fixed relative to the intercostal element 18. A pair of ball and socket bearings $2a$ and $2c$ are mounted to the upper forward body part 12, while a ball and socket bearing $2e$ is mounted to the upper rearward body part 16.

The end effector for performing a maintenance function and the means for scanning that end effector in a chordwise direction are not shown in FIG. 2, except for a portion of a guide rod 20 integrally formed with a mounting plate 30 that is fastened to the upper forward body part 12. In particular, the slider which slides on the guide rod 20 and carries the end effector is not shown. Also, a drive roller and a follower roller in contact with the leading edge of the airfoil-shaped body 100 and a drive motor for driving rotation of the drive roller (similar to elements 120, 122 and 124 shown in FIG. 1) are not shown in FIG. 2 to reduce clutter in the drawing. However, it should be understood that the embodiment shown in FIG. 2 comprises at least one drive motor/drive roller for self-propulsion and means for scanning an end effector in a chordwise direction even though such components are not shown. This convention will also be adopted in FIGS. 3, 4A-C, 5A-C, and 6A-C.

Still referring to FIG. 2, the chassis of the blade crawler also comprises a lower forward body part 14 which is telescopically coupled to the upper forward body part 12 for manually adjusting the vertical distance separating opposing horizontal arms of the upper and lower forward body parts during mounting of the crawler on the airfoil-shaped body 100. A pair of ball and socket bearings $2b$ and $2d$ are mounted to the lower forward body part 14. The vertical distance separating opposing horizontal arms of the upper and lower forward body parts will be selected so that the opposing pairs of ball and socket bearings $2a$-$2b$ and $2c$-$2d$ respectively contact the upper and lower surfaces of the airfoil-shaped body 100. When the horizontal arms of the upper and lower forward body parts are separated by an optimum vertical distance, a set screw or other locking means can be used to prevent further relative movement of the upper and lower forward body parts during crawler operation. Optionally, each of ball and socket bearings $2a$-$2d$ may be slidably coupled to the upper and lower forward body parts and may include a respective internal compression spring for urging ball and socket bearings $2a$-$2d$ toward the respective surfaces of the airfoil-shaped body 100.

The chassis further comprises a lower rearward body part 22 which supports a ball and socket bearing $2f$ (both of which are drawn using dashed lines to indicate they are below and hidden from view by the airfoil-shaped body 100). Preferably ball and socket bearing $2f$ opposes ball and socket bearing $2e$, which is mounted to upper rearward body part 16. Optionally, ball and socket bearings $2e$ and $2f$ may be slidably coupled to the upper and lower rearward body parts respectively and may include a respective internal compression spring for urging ball and socket bearings $2e$ and $2f$ toward the upper and lower surfaces respectively of airfoil-shaped body 100.

The lower rearward body part 22 depends from the upper rearward body part 16. The upper and lower rearward body parts are connected by an assembly comprising an upper axle support 24 connected to upper rearward body part 16, a lower axle support 28 connected to lower rearward body part 22, and an axle 25 whose opposing ends are supported by the upper and lower axle supports so that the axis of axle 25 is generally vertical. The vertical separation between the two rearward body parts may be adjustable by any conventional means. For example, the lower axle support 28 can be slidably coupled to the lower end of axle 25, but lockable in place after a manual adjustment has been made. The vertical position of the lower axle support 28 could be changed by unlocking the lower axle support 28, sliding it vertically along axle 25, and then locking lower axle support 28 at an optimum vertical position whereat ball and socket bearings $2e$ and $2f$ contact the upper and lower surfaces respectively of airfoil-shaped body 100.

In accordance with the embodiment shown in FIG. 2, a roller 26 is rotatably mounted on axle 25. The roller 26 is in contact with and rolls along the trailing edge 96 of the airfoil-shaped body 100. In one implementation, roller 26 comprises a roller bearing having an inner race attached to axle 25 and an outer race rotatable relative to the inner race. However, as disclosed in detail below, other types of rollers engaging the blade trailing edge 96 should be used in cases wherein the roller is expected to traverse over trailing edge protrusions.

In accordance with an alternative embodiment, the axle 25 may be replaced by a shaft coupled to a motor housed inside the rearward body part 16 for driving rotation of roller 26. In this situation, the motor driving rotation of roller 26 is slaved to the drive motor that drives rotation of the drive roller in contact with the leading edge of the airfoil-shaped body 100.

The ball and socket bearings 2a-2f enable motion of the apparatus along complex-shaped blades (i.e., in a spanwise direction) without causing misdirection. The ball and socket bearings can be similar to any one of a plurality of commercially available types of ball and socket bearings, such as those used in the design of office furniture. When ball and socket bearings are used instead of alignment wheel, a nearly frictionless omni-directional alignment device is provided. The ball and socket bearings 2a-2f maintain positive alignment of the crawler with the blade features without causing misdirection, so that complex-curvature blades with twist, camber and sweep can be accommodated.

FIG. 3 shows portions of a blade crawler having a plurality of air pads 4a through 4f for maintaining alignment on an airfoil-shaped body 100. For the purpose of illustration only, it will be assumed that the chassis of the blade crawler shown in FIG. 3 has the same structure as that of the chassis shown in FIG. 2 so that the detailed description of such chassis structure need not be repeated.

In accordance with the embodiment shown in FIG. 3, a pair of air pads 4a and 4c are mounted to the upper forward body part 12, while an air pad 4e is mounted to the upper rearward body part 16. Similarly, pair of air pads 4b and 4d are mounted to the lower forward body part 14, while an air pad 4f (indicated by dashed lines in FIG. 3 because it is hidden below the airfoil-shaped body 100) is mounted to the lower rearward body part 22. Optionally, each of air pads 4a-4d may be slidably coupled to the upper and lower forward body parts and may include a respective internal compression spring for urging air pads 4a-4d toward the respective surfaces of the airfoil-shaped body 100. Likewise air pads 4e and 4f may be slidably coupled to the upper and lower rearward body parts respectively and may include a respective internal compression spring for urging air pads 4e and 4f toward the upper and lower surfaces respectively of airfoil-shaped body 100.

The air pads 4a-4f enable motion of the apparatus along complex-shaped blades without causing misdirection. Each air pad is configured with an edge seal (usually comprised of rubber material) that lines the perimeter of a hard pad that can be mounted on a swivel. The air pad alignment elements can be configured with either several moderately sized pads or with a single larger pad that covers a broader surface area. When high pressure air is forced into the manifold created by the edge seal between the pad and blade surface, a respective cushion of air is produced between each air pad and the airfoil surface, creating a nearly frictionless omni-directional alignment feature. The air pads 4a-4f maintain positive alignment of the crawler with the blade features without causing misdirection, so that complex-curvature blades with twist, camber and sweep can be accommodated.

In accordance with a further enhancement, the blade crawler is provided with the ability to autonomously traverse over trailing edge protrusions during spanwise motion without loss of functionality. This is accomplished by equipping the crawler with any one of three types of devices: (1) an oversized-diameter roller; (2) a semi-flexible roller; or (3) a dual-roller arrangement. Respective embodiments of these devices will now be described with reference to FIGS. 4A-4C, 5A-5C, and 6A-6C respectively. In each of these embodiments, the respective device for traversing over a trim tab 98 is employed in conjunction with ball and socket bearings of the type shown in FIG. 2. However, it should be appreciated that these devices could also be employed in conjunction with air pads of the type shown in FIG. 3. In accordance with further alternatives, the devices disclosed below could be used with alignment mechanisms other than ball and socket bearings or air pads.

In each of FIGS. 4A-4C, 5A-5C, and 6A-6C, means for moving the crawler in a spanwise direction (continuously or incrementally), an end effector for performing a maintenance function, and means for moving that end effector in a chordwise direction (continuously or incrementally) are not shown. In accordance with a further convention adopted herein, in each of FIGS. 4A-4C, 5A-5C, and 6A-6C, the airfoil-shaped body 100, the trim tab 98 at the trailing edge 96 of airfoil-shaped body 100, the upper rearward body part 16 and the ball and socket bearing 2e have been drawn in dashed lines to better illustrate the devices for traversing over a trim tab 98 and components of the crawler (such as ball and socket bearing 2f and lower rearward body part 22) that would otherwise be hidden by the airfoil-shaped body 100 in the views presented.

Figure 4A:
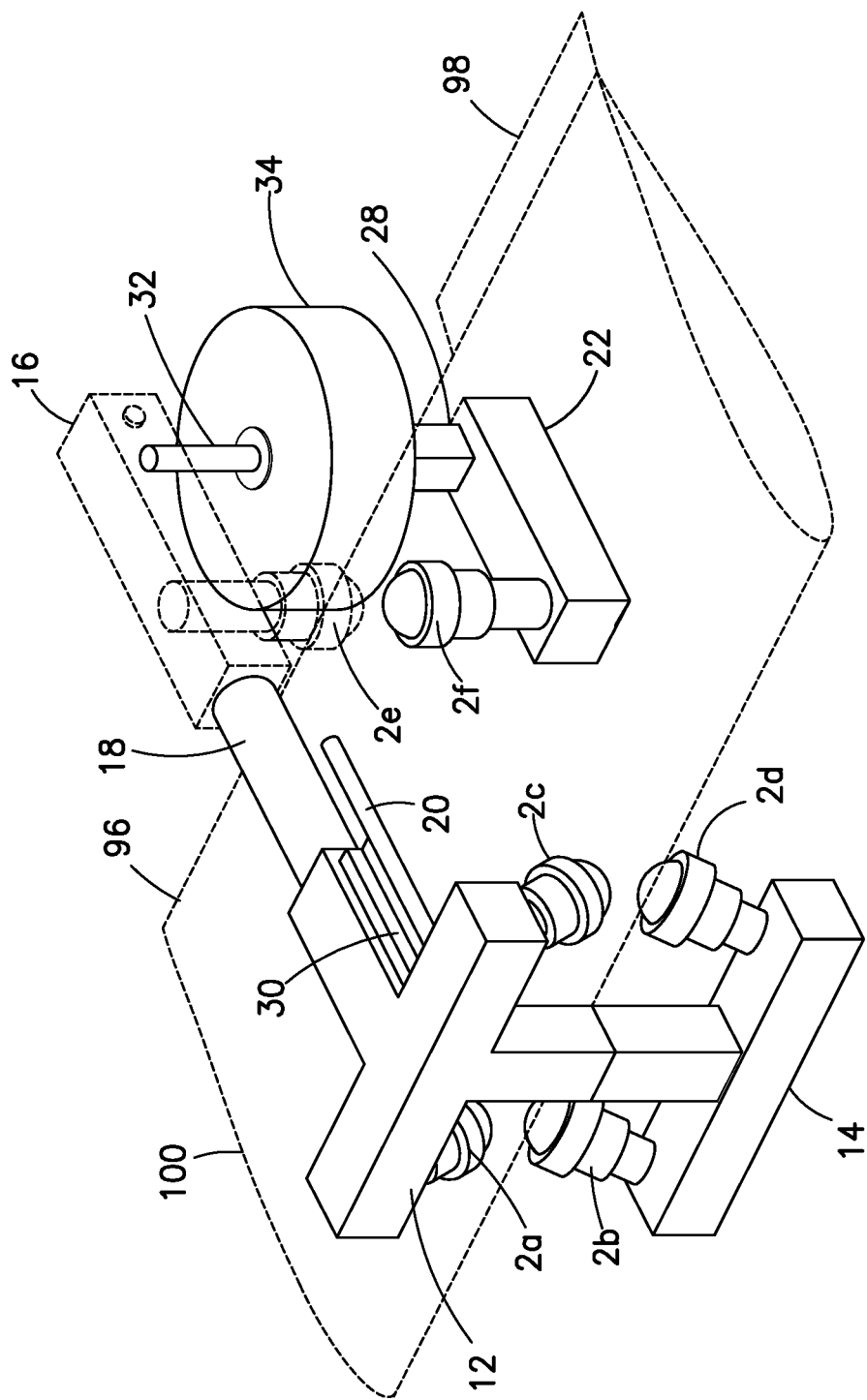
FIGS. 4A through 4C are isometric views showing some components of a blade crawler having a plurality of ball and socket bearings for maintaining alignment on the blade component and having an oversized-diameter roller capable of traversing over trailing edge protrusions. These drawings respectively show the oversized-diameter roller approaching a trailing edge protrusion (FIG. 4A); climbing the trailing edge protrusion (FIG. 4B); and accommodating the trailing edge protrusion (FIG. 4C). Again, the end effector for performing a maintenance function and the means for scanning that end effector in a chordwise direction are not shown.
Figure 4B:
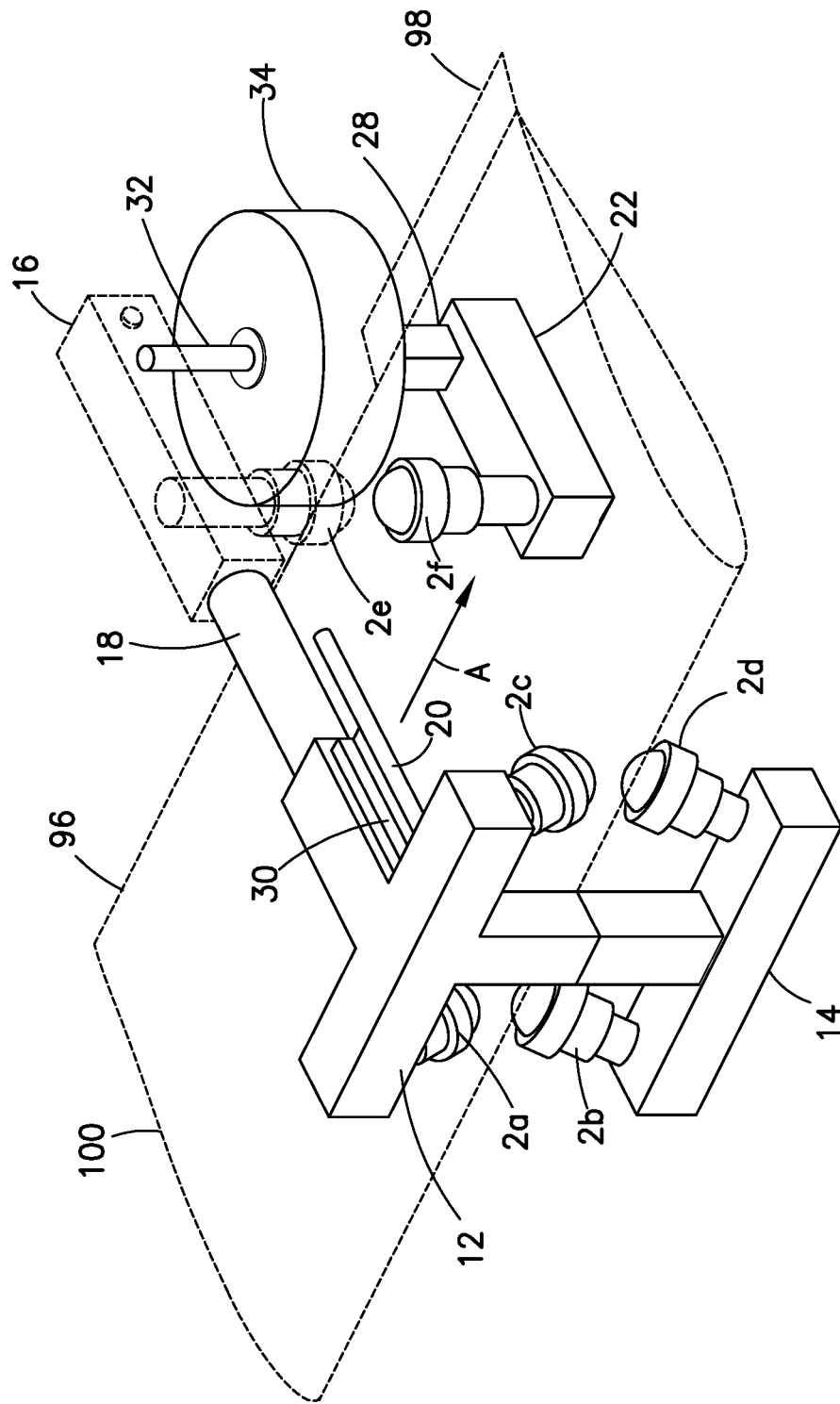
Figure 4C:
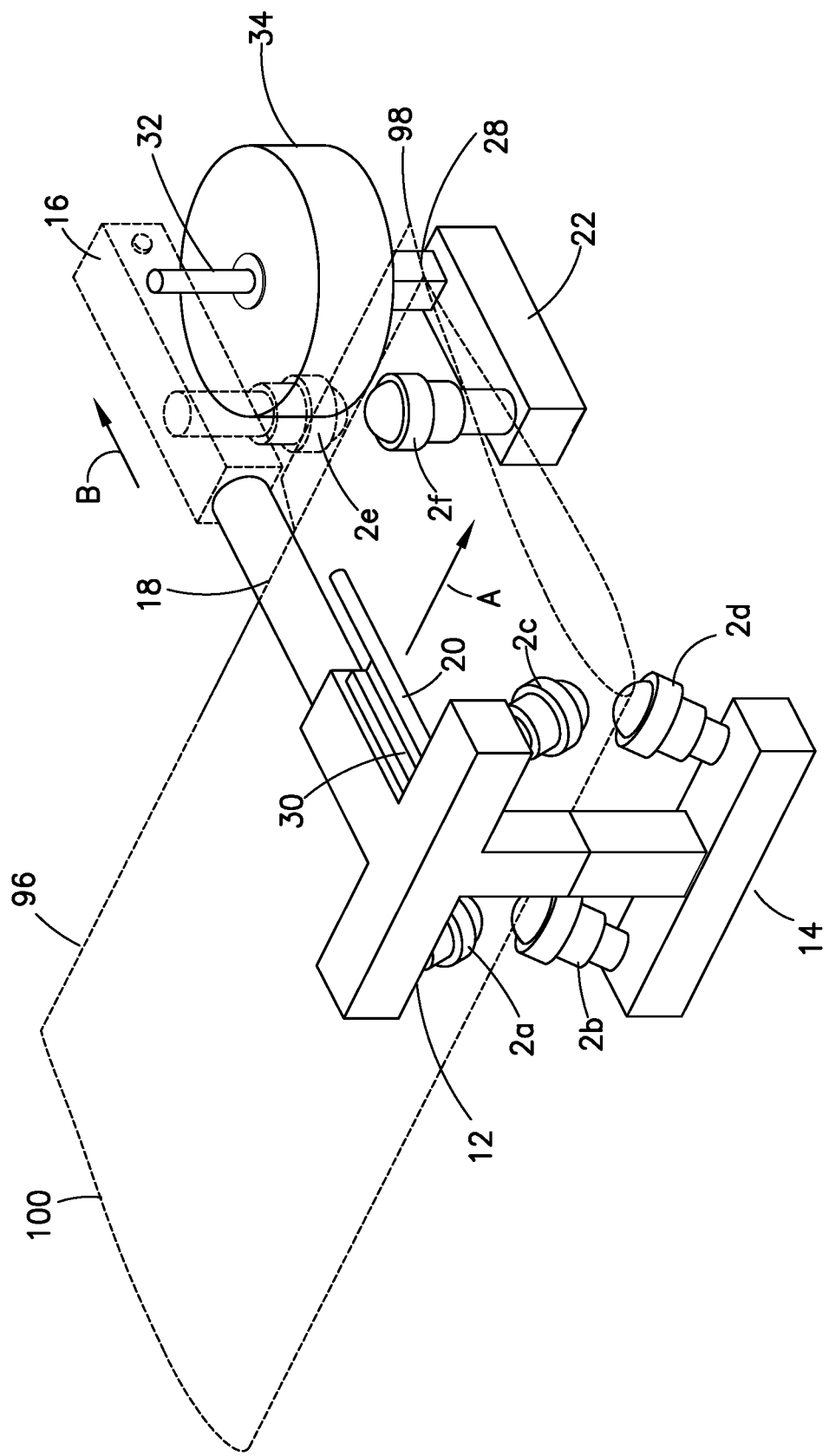

FIGS. 4A through 4C show some components of a blade crawler having a plurality of ball and socket bearings 2a-2f for maintaining alignment on the blade component and having a rigid oversized-diameter roller 34 capable of rolling over a trailing edge protrusion. These drawings respectively show the oversized-diameter roller 34 approaching a trim tab 98 (FIG. 4A); climbing the trim tab 98 (FIG. 4B); and accommodating the trim tab 98 (FIG. 4C). The oversized-diameter roller 34 is adjustably positioned so that its outer peripheral surface is in contact with trailing edge 96 of the airfoil-shaped body 100.

In the implementation seen in FIG. 4A, the oversized-diameter roller 34 is rotatably mounted on an axle 32 whose opposing ends are supported by an upper axle support (not shown) disposed inside the rearward body part 16 and a lower axle support 28 so that the axis of axle 32 is generally vertical. As the crawler moves in a spanwise direction, the oversized-diameter roller 34 will roll along the trailing edge 96 of the airfoil-shaped body 100. In some implementations, a second drive motor slaved to the drive motor that is driving spanwise motion of the crawler may be employed to drive the oversized-diameter roller 34 along the trailing edge 96 and over the trim tab 98 protruding from the trailing edge 96 of the airfoil-shaped body 100.

FIG. 4B shows the crawler moving in a spanwise direction (indicated by arrow A) at the instant in time when the outer peripheral surface of the oversized-diameter roller 34 impinges on a corner at the trailing edge of the trim tab 98. The radius of the oversized-diameter roller 34 is sufficiently greater than the width of the trim tab 98 such that the oversized-diameter roller 34 will roll over the impinging corner as the crawler moves further in the spanwise direction A. When this happens, the impinging corner of trim tab 98 will exert a reaction force on the outer peripheral surface of the oversized-diameter roller 34 that has both a chordwise component and a spanwise component.

In accordance with one embodiment, the rearward body part 16 will start moving rearward along the intercostal element 18 in response to the chordwise component of the reaction force exerted by the trim tab on the oversized-diameter roller 34 exceeding a threshold. The rearward motion of the rearward body part 16 allows the oversized-diameter roller 34 to climb over the impinging corner of the trim tab 98. This rearward motion of the rearward body part 16 is indicated by arrow B in FIG. 4C, which shows the situation after the oversized-diameter roller 34 climbs the trim tab 98 and the outer peripheral surface of the oversized-diameter roller 34 is now in contact with the trailing edge of the trim tab 98. As the crawler moves further in the spanwise direction A, the oversized-diameter roller 34 rolls along the trailing edge of the trim tab 98. When the oversized-diameter roller 34 reaches the end of the trim tab as the crawler continues to move in the spanwise direction A, the oversized-diameter roller 34 will roll off of the trim tab and back onto the trailing edge 96 of the airfoil-shaped body 100 as the rearward body part 16 moves in a forward direction opposite to the direction indicated by arrow B in FIG. 4C.

In accordance with one embodiment, a tension spring (not shown in FIGS. 4A-4C) housed in rearward body part 16 provides sufficient force to return the rearward body part 16 to its starting chordwise position. That tension spring is extended when the oversized-diameter roller 34 climbs onto the trim tab 98 and then retracts when the oversized-diameter roller 34 climbs off of the trim tab 98.

Figure 13:
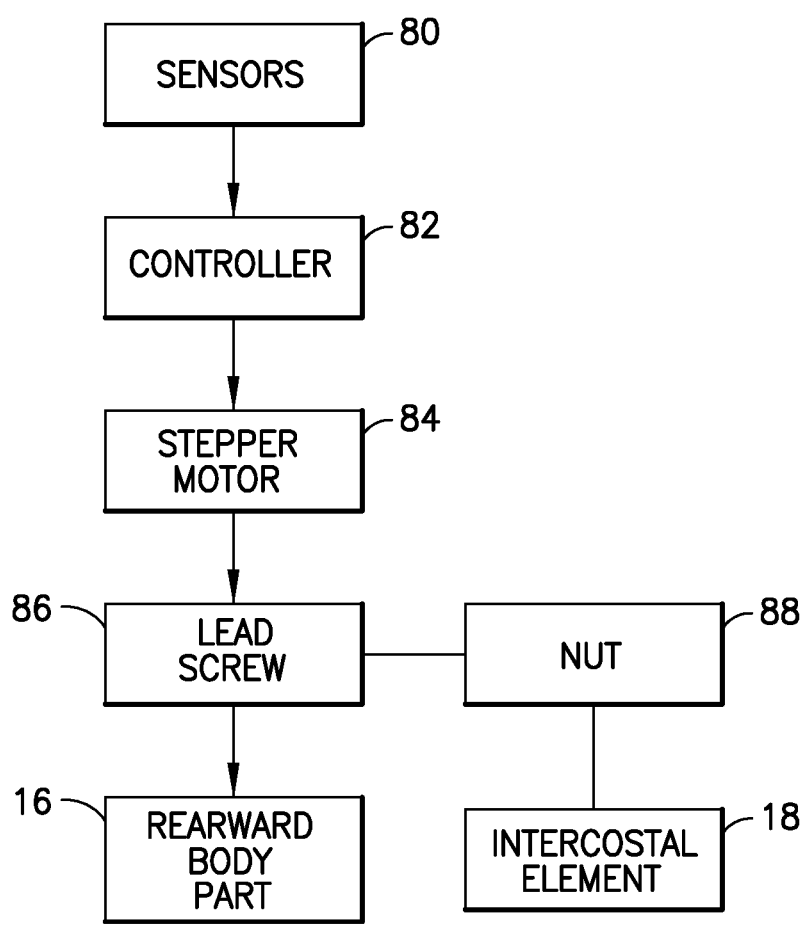
FIG. 13 is a block diagram identifying components of a crawler comprising a subsystem for causing chordwise movement of a device for traversing a protrusion of a trailing edge of an airfoil-shaped body.

In accordance with an alternative embodiment having the components identified in FIG. 13, the rearward body part 16 may house or carry a stepper motor 84 that drives a lead screw 86 for controlling the chordwise position of the rearward body part 16 relative to the intercostal element 18. The lead screw 86 is threadably coupled to a nut 88 attached to the intercostal element 18. The stepper motor 84 would be activated to move the rearward body part 16 rearward in response to a signal from a sensor 80 indicating that the oversized-diameter roller 34 was approaching a corner of the trim tab 98. The sensor signal is received by a controller 82 (such as the control computer described above) located at an operations command center. The controller 82 then sends a rearward displacement command to a microprocessor that is part of the stepper motor. Another sensor 80 would output a signal when the axis of the oversized-diameter roller 34 reaches a spanwise position corresponding to the end of the trim tab. In the latter instance, controller 82 will send a forward displacement command to the stepper motor.

In accordance with a further alternative embodiment, movement of the rearward body part 16 in a chordwise direction could be actuated by a solenoid.

Because the oversized-diameter roller 34 can roll over trailing edge protrusions, it is possible for the crawler to accommodate blades with trim tabs, trim tab covers, and other trailing edge irregularities.

Figure 5A:
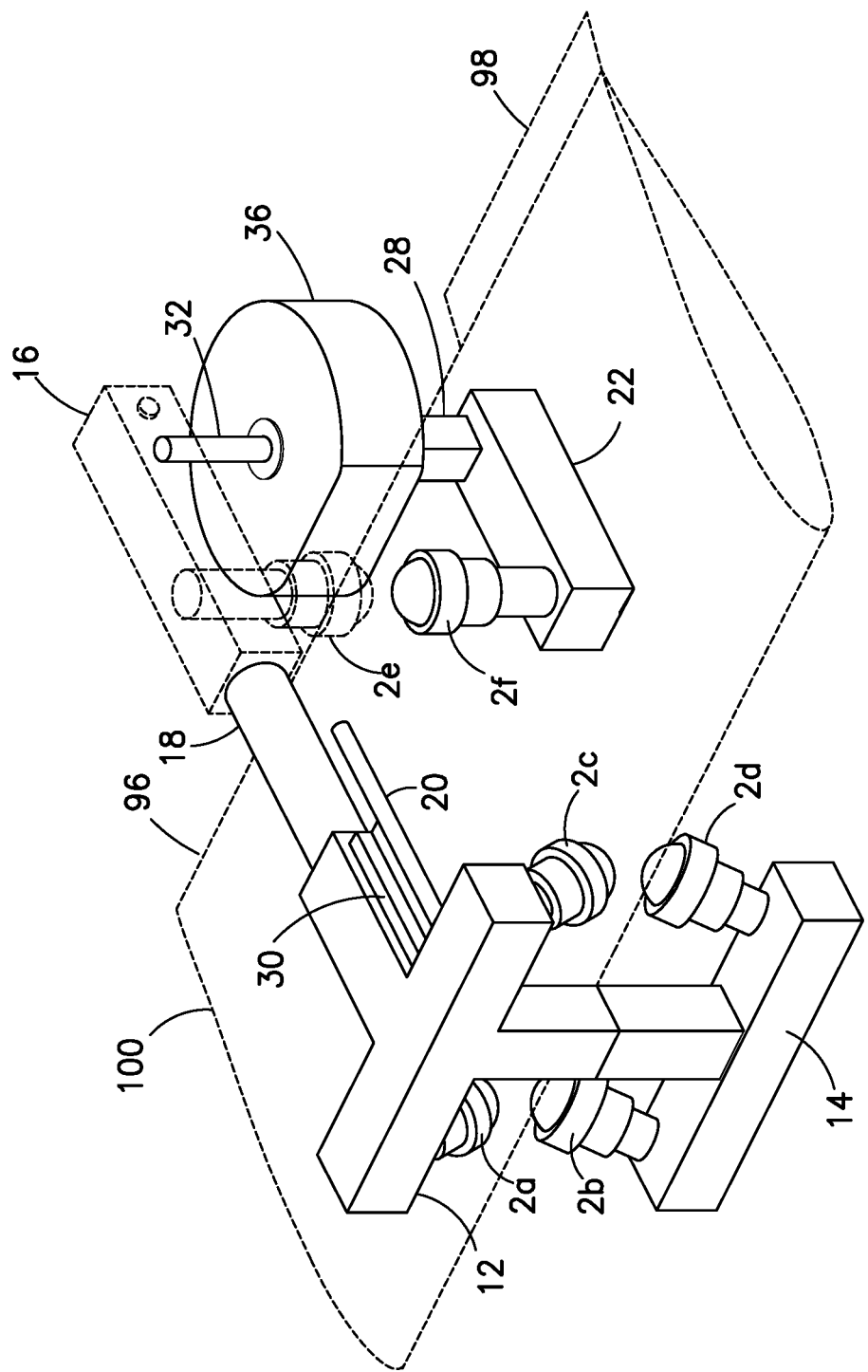
FIGS. 5A through 5C are isometric views showing some components of a blade crawler having a plurality of ball and socket bearings for maintaining alignment on the blade component and having a semi-flexible roller capable of traversing over trailing edge protrusions while the blade crawler is in a chassis displacement mode. These drawings respectively show the semi-flexible roller approaching a trailing edge protrusion (FIG. 5A); climbing the trailing edge protrusion (FIG. 5B) in a protrusion climbing mode; and accommodating the trailing edge protrusion (FIG. 5C). Again, the end effector for performing a maintenance function and the means for scanning that end effector in a chordwise direction are not shown.
Figure 5B:
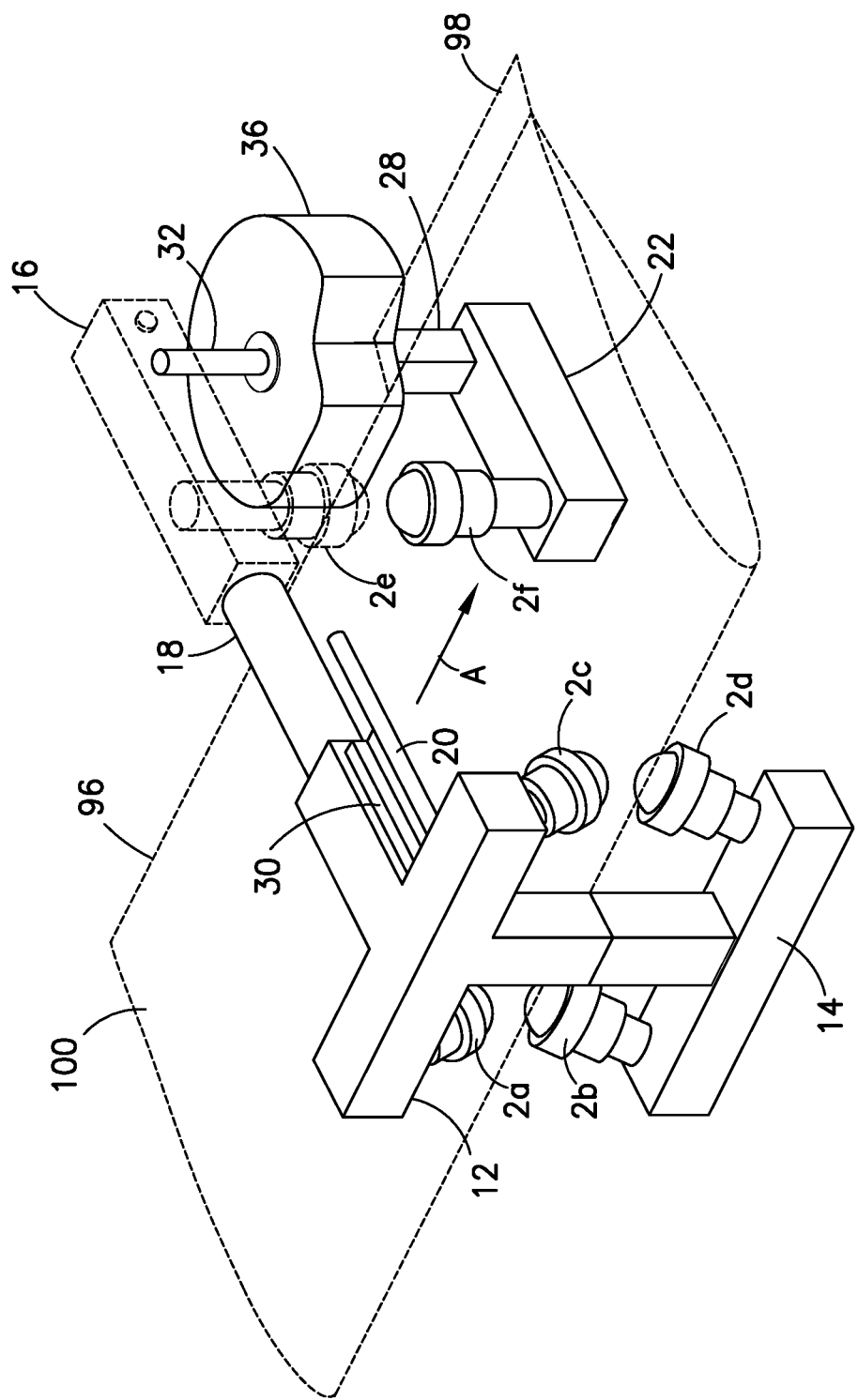
Figure 5C:
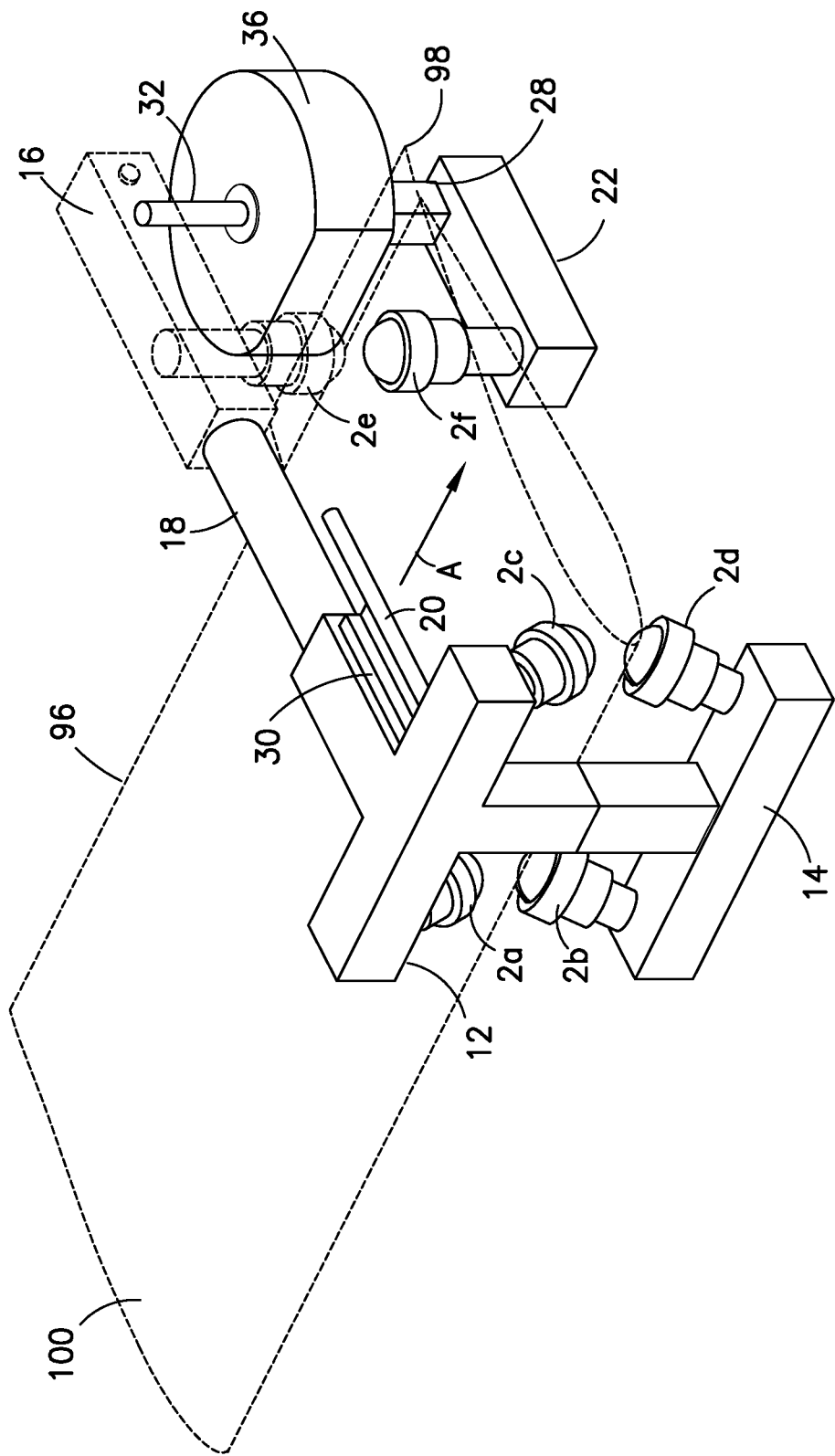

FIGS. 5A through 5C show some components of a blade crawler having a plurality of ball and socket bearings 2a-2f for maintaining alignment on the blade component and having a semi-flexible roller 36 capable of rolling over a trailing edge protrusion. These drawings respectively show the semi-flexible roller 36 approaching a trim tab 98 (FIG. 5A); climbing the trim tab 98 (FIG. 5B); and accommodating the trim tab 98 (FIG. 5C). The semi-flexible roller 36 is adjustably positioned so that it compresses to an optimum degree in response to the reactive force exerted by the trailing edge 96 of the airfoil-shaped body 100. To simplify these drawings, varying deformation of the semi-flexible roller material above and below its line of contact with the trailing edge 96 is not shown.

In the implementation seen in FIG. 5A, the semi-flexible roller 36 is rotatably mounted on an axle 32 whose opposing ends are supported by an upper axle support (not shown) disposed inside the rearward body part 16 and a lower axle support 28 so that the axis of axle 32 is generally vertical. The semi-flexible roller 36 may, for example, comprise a wheel of soft elastomeric foam or semi-rigid foam adhered or attached to a bushing, which bushing is rotatably mounted on axle 32. As ideally depicted in FIG. 5A, the semi-flexible roller 36 is deformed and/or compressed due to its contact with the trailing edge 96, including a contacted portion that also conforms to the shape of the trailing edge 96. In practice, semi-flexible material above and below the trailing edge will not deform to the same extent as the portion in contact with the trailing. The result (not shown in FIG. 5A) would be that the compressed portion of the semi-flexible roller could form a V-shaped groove which may assist crawler alignment on the airfoil-shaped body 100.

As the crawler moves in a spanwise direction, the semi-flexible roller 36 will roll along the trailing edge 96. In some implementations, a drive motor slaved to the drive motor that is driving spanwise motion of the crawler may be employed to drive the semi-flexible roller 36 along the trailing edge 96 and over the trim tab 98.

FIG. 5B shows the crawler moving in a spanwise direction (indicated by arrow A) at an instant in time when the semi-flexible roller 36 is being deformed by a corner at the trailing edge of the trim tab 98. The semi-flexible roller 36 has the ability to traverse over the impinging corner as the crawler moves further in the spanwise direction A.

In accordance with one embodiment, a sensor (not shown) detects when the semi-flexible roller 36 is approaching the position shown in FIG. 5B and sends a signal to a controller. In response to that signal, the controller commands an actuator to move the rearward body part 16 in a rearward direction, which displacement in turn causes the axle 32 to displace rearwardly. This rearward displacement of axle 32 allows the semi-flexible roller 36 to climb over the corner of the trim tab 98. As the crawler moves further in the spanwise direction A, the semi-flexible roller 36 rolls along and accommodates the trailing edge of the trim tab 98 as shown in FIG. 5C. Rearward displacement of the rearward body part 16 may be actuated using any of the means previously described with reference to the embodiment having an oversized-diameter roller.

Figure 6A:
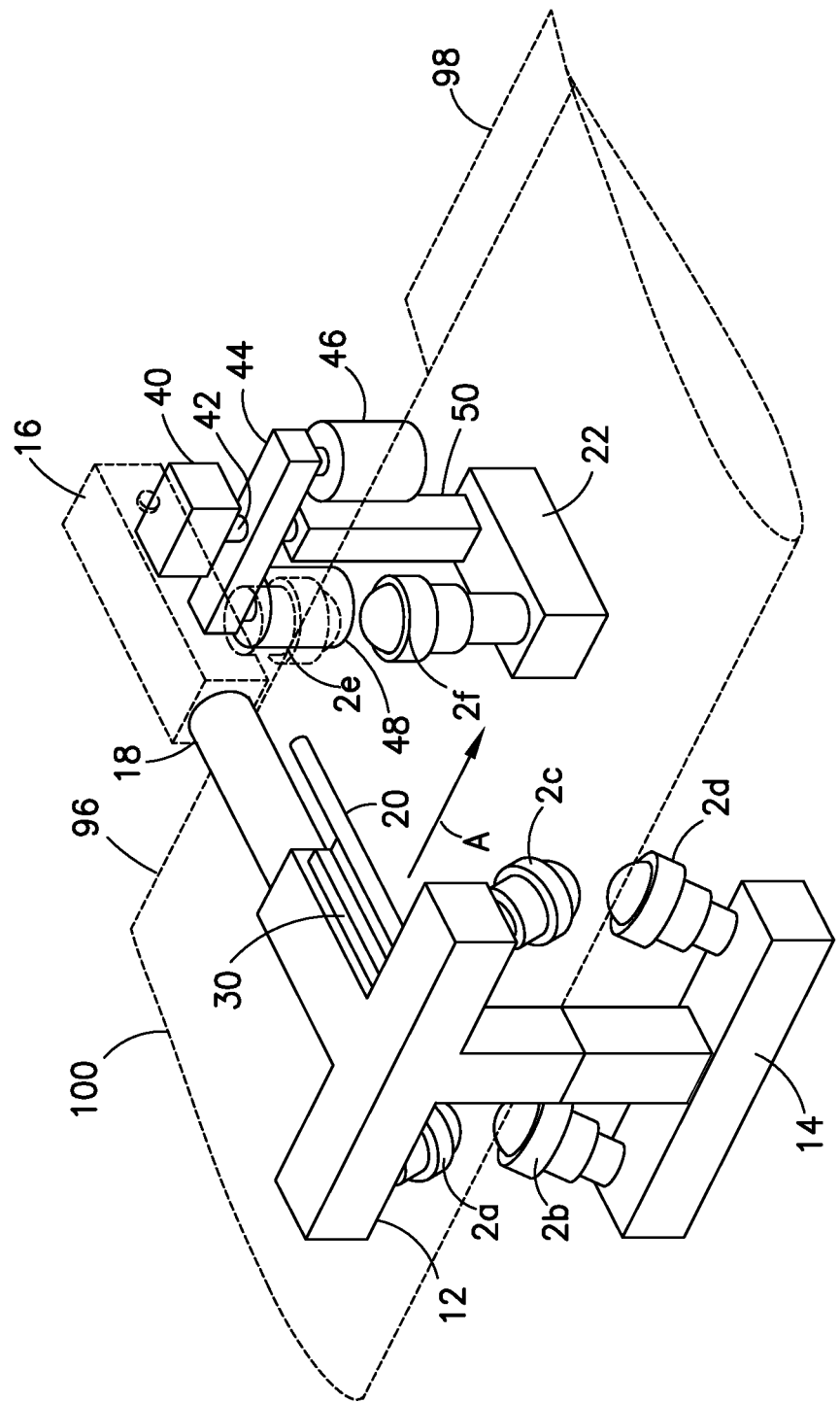
FIGS. 6A through 6C are isometric views showing some components of a blade crawler having a plurality of ball and socket bearings for maintaining alignment on the blade component and having a dual-roller follower arrangement capable of traversing over trailing edge protrusions. These drawings respectively show the dual-roller arrangement approaching a trailing edge protrusion (FIG. 6A); climbing the trailing edge protrusion (FIG. 6B); and accommodating the trailing edge protrusion (FIG. 6C). Again, the end effector for performing a maintenance function and the means for scanning that end effector in a chordwise direction are not shown.
Figure 6B:
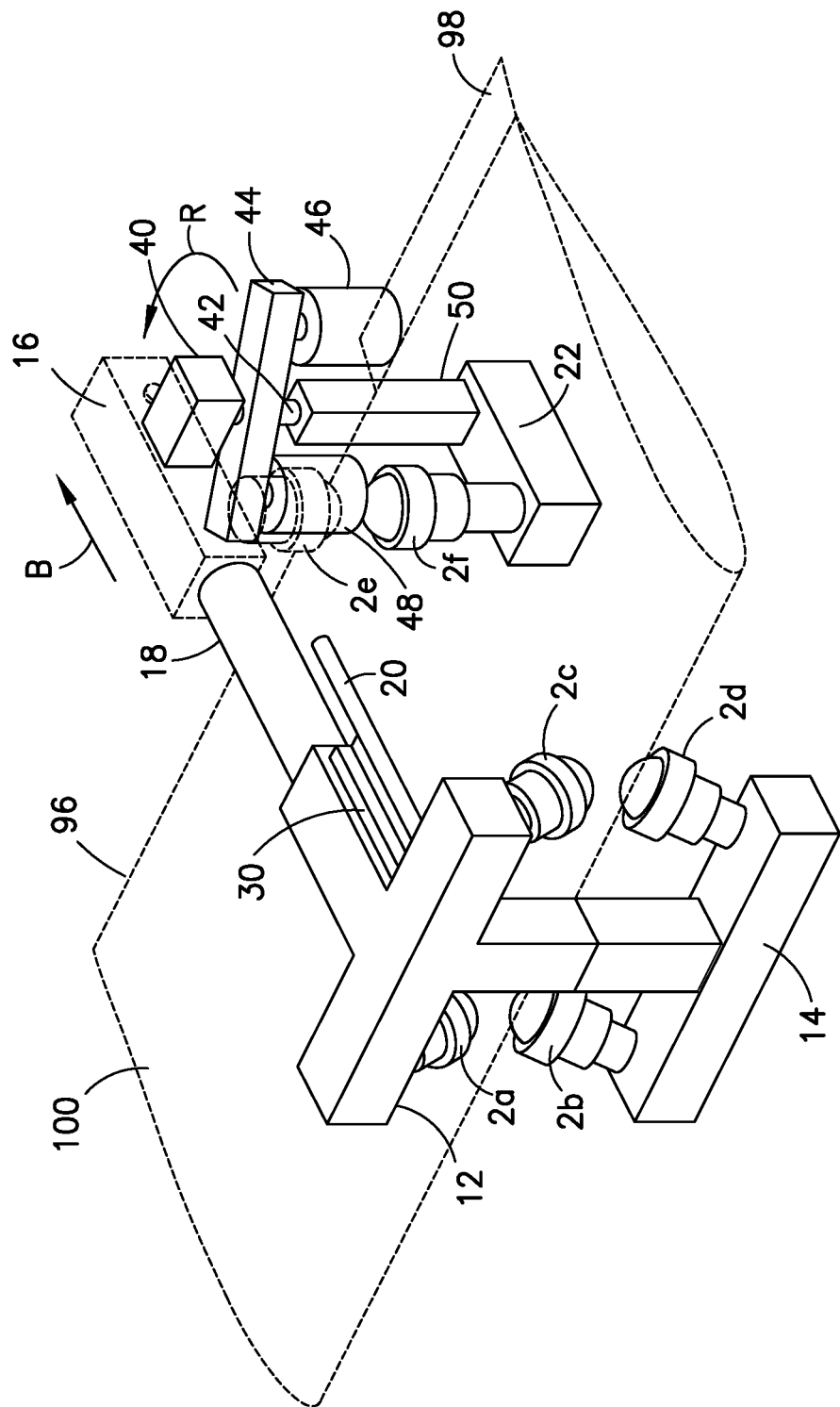
Figure 6C:
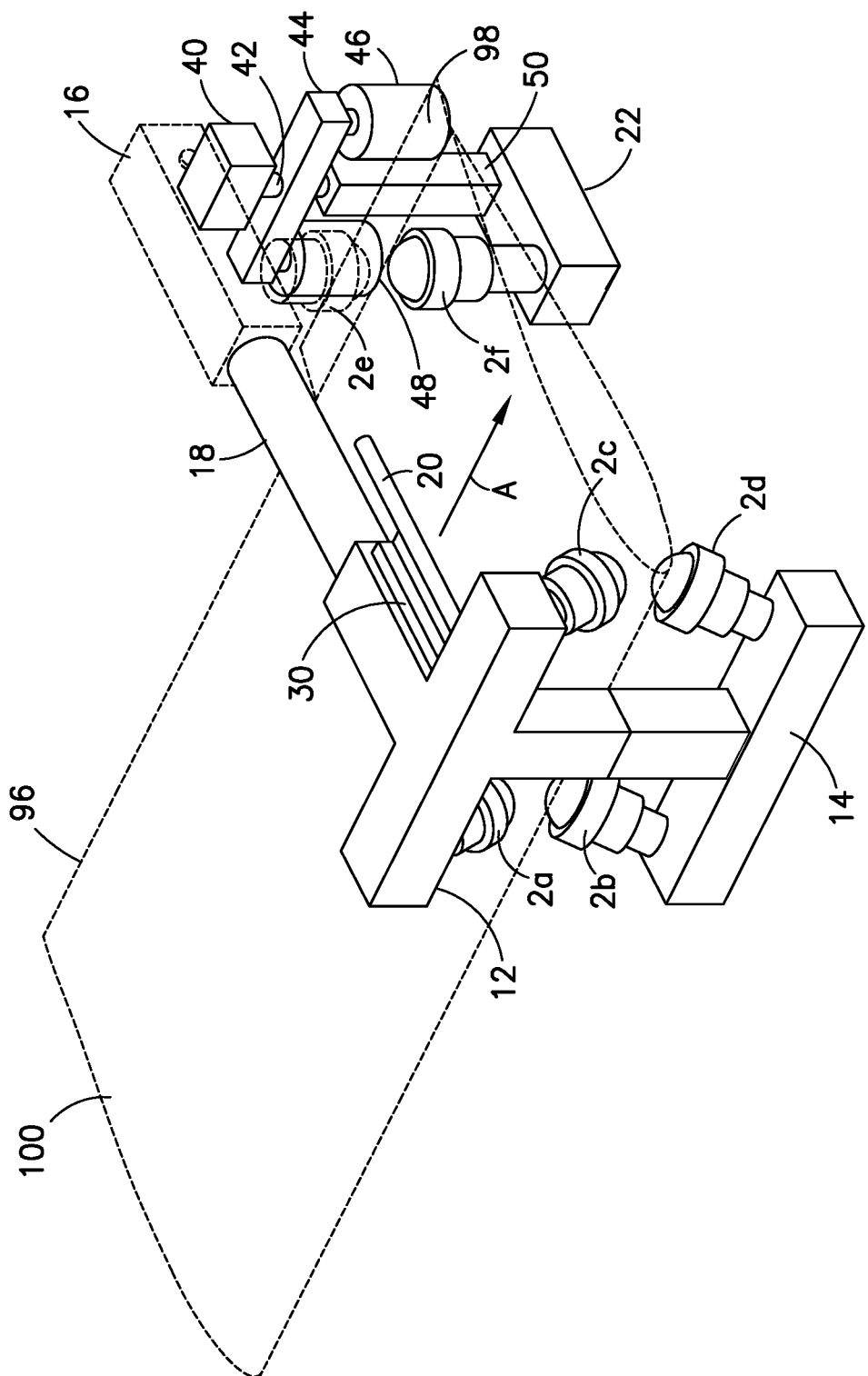

FIGS. 6A through 6C show some components of a blade crawler having a plurality of ball and socket bearings 2a-2f for maintaining alignment on the blade component and having a dual-roller arrangement capable of traversing over a trailing edge protrusion. These drawings respectively show the dual-roller arrangement approaching a trim tab 98 (FIG. 6A); climbing the trim tab 98 (FIG. 6B); and accommodating the trim tab 98 (FIG. 6C). The chordwise position of the dual-roller arrangement is determined by the chordwise position of the rearward body part 16 relative to the intercostal element 18, which is adjustable as previously described.

Referring to FIG. 6A, the dual-roller arrangement is rotatably mounted on an axle 42 (by means of bearings not shown) having one end supported by a base block 40 attached to the upper rearward body part 16 and another end attached to one end of a support member 50 so that the axis of axle 42 is generally vertical. The other end of support member 50 is connected to the lower rearward body part 22. The dual-roller arrangement comprises a pivoting cross beam 44 rotatably mounted at its midpoint (by bearings not shown) to the axle 42. The opposing ends of the pivoting cross beam 44 support rollers 46 and 48 respectively. Preferably the axis of axle 42 is at the midpoint between the axes of rotation of the rollers 46 and 48. When scanning a portion of the airfoil-shaped body 100 that has no trailing edge protrusions (as depicted in FIG. 6A), the rearward body part 16 is positioned so that both rollers 46 and 48 are in contact with the trailing edge 96 of the airfoil-shaped body 100. In some implementations, a drive motor slaved to the drive motor that is driving spanwise motion of the crawler may be employed to drive one of the rollers 46 and 48 along the trailing edge 96.

Still referring to FIG. 6A, when the leading roller 46 approaches the trim tab 98 during spanwise motion of the crawler, a sensor (not shown) signals that a protrusion climbing mode should be initiated. In the protrusion climbing mode, the rearward body part 16 will be displaced rearward by a distance W that is equal to the width of the trim tab 98. Since the axis of the axle 42 is fixed relative to the rearward body part 16, the axle 42 is also displaced rearward by a distance W. The protrusion climbing mode in accordance with one implementation may have three phases.

In the first phase of the protrusion climbing mode, the motor (not shown in FIGS. 6A-6C) that drives chordwise motion of the rearward body part 16 is activated to displace the rearward body part 16 in a rearward direction (indicated by arrow B in FIG. 6B) and a motor (not shown in FIGS. 6A-6C) that drives rotation of the dual roller arrangement in a counterclockwise direction (indicated by arrow R) is activated. Thus the pivoting cross beam 44 rotates while the axle 42 displaces rearwardly. The rotation of pivoting cross beam 44 can be coordinated so that, at the end of a first leg of the shaft's planned rearward displacement (i.e., after a displacement ½W), the pivoting cross beam 44 will have pivoted by an angle such that the trailing roller 48 remains in contact with the trailing edge 96 of the airfoil-shaped body 100 while the leading roller 46 is displaced by the distance W. (This relationship is based on the assumption that the rollers 46 and 48 have equal radii and that the axis of axle 42 is at the midpoint between the axes of the rollers 46 and 48.) This rearward displacement by a distance W enables the leading roller 46 to climb over the corner and onto the trailing edge of trim tab 98 (as shown in FIG. 6B) as the crawler moves in the spanwise direction.

In the second phase of the protrusion climbing mode, the motor that drives chordwise motion of the rearward body part 16 and the motor that drives rotation of the pivoting cross beam 44 are deactivated. During further spanwise movement of the crawler, the leading roller 46 will roll along the trailing edge of the trim tab 98 while the trailing roller 48 rolls along trailing edge 96 of the airfoil-shaped body 100. When the trailing roller 48 approaches the trim tab 98, this event is also detected by a sensor and the third phase of the protrusion climbing mode is then initiated by the controller.

In the third phase of the protrusion climbing mode, the motor that drives chordwise motion of the rearward body part 16 is activated to displace the rearward body part 16 further in a rearward direction (i.e., increasing the rearward displacement from ½W to W) and the motor 40 that drives rotation of the pivoting cross beam 44 is activated concurrently to rotate the pivoting cross beam 44 in a clockwise direction (i.e., opposite to the direction indicated by arrow R in FIG. 6B). As the axle 42 displaces further in a rearward direction, the motor that drives rotation of the pivoting cross beam 44 causes the pivoting cross beam 44 to rotate in the clockwise direction. The displacement of axle 42 and rotation of pivoting cross beam 44 are coordinated so that, at the end of the second leg of the planned (now completed) rearward displacement of axle 42 (i.e., after a total displacement W), the pivoting cross beam 44 will have pivoted by the same angle as in the first phase but in the opposite direction such that the leading roller 46 remains in contact with the trailing edge of the trim tab 98 while the trailing roller 48 has now been displaced by the distance W. This rearward displacement by a distance W enables the trailing roller 48 to climb over the corner and onto the trailing edge of trim tab 98 during spanwise motion of the crawler.

While both rollers 46 and 48 are in contact with the trailing edge of the trim tab 98 (as seen in FIG. 6C), the spanwise motion (continuous or incremental) of the crawler may continue. When the leading roller 46 reaches the end of the trim tab 98, the controller will then initiate a protrusion dismounting mode during which the rearward body part 16 displaces in a forward direction. In a manner similar to what occurred in the protrusion climbing mode, the protrusion dismounting mode has respective phases during which the pivoting cross beam 44 is first rotated in a clockwise direction and then in a counterclockwise direction. Upon completion of the dismounting procedure, the rollers 46 and 48 will again be in contact with the trailing edge 96 of the airfoil-shaped body 100.

Figure 7:
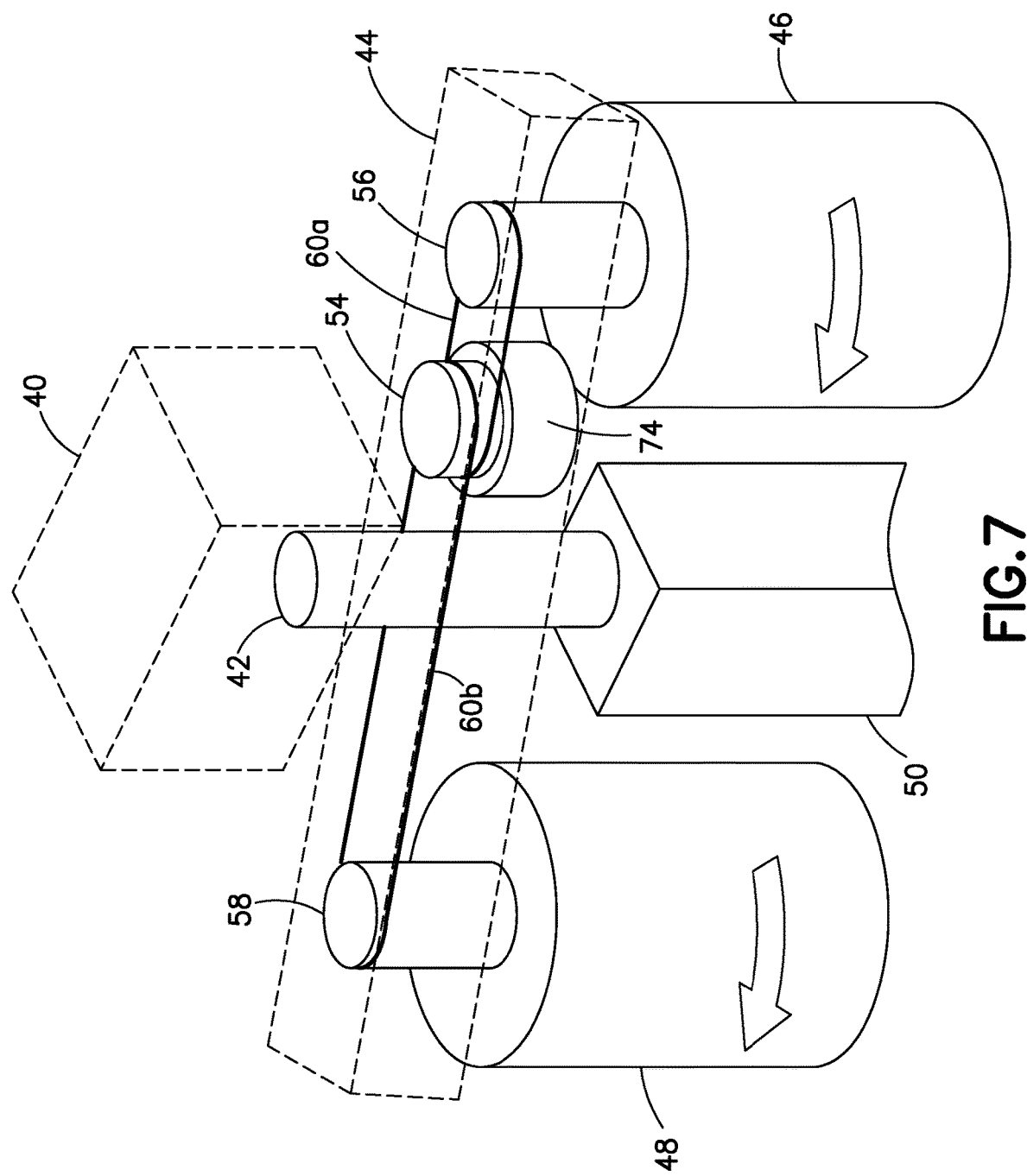
FIGS. 7 through 10 are diagrams representing isometric views of respective embodiments of the dual-roller arrangement depicted in FIGS. 6A-6C.

FIG. 7 is a diagram representing an isometric view of a first embodiment of the dual-roller arrangement depicted in FIGS. 6A-6C. In this embodiment, instead of the pivoting cross beam 44 being driven to rotate about axle 42 by a motor, the rollers 46 and 48 are driven to rotate (indicated by respective curved arrows) by a drive system housed inside the pivoting cross beam 44. This drive system comprises a roller drive motor 74 having an output shaft (not shown in FIG. 7) connected to a drive pulley 54. The drive pulley 54 in turn is coupled to follower pulleys 56 and 58 by respective drive belts (or chains) 60a and 60b. The leading roller 46 is fixedly coupled to the follower pulley 56 for rotation therewith. Similarly, the trailing roller 48 is fixedly coupled to the follower pulley 58 for rotation therewith. Accordingly, roller drive motor 74 can be activated to drive concurrent rotation of the leading and trailing rollers 46 and 48 along the trailing edge of the blade. Transiting over trailing edge obstacles is accomplished by the leading and trailing rollers 46 and 48 actively driving over the contours. In accordance with this arrangement, the pivoting cross beam 44 will rotate about axle 42 in different directions as the leading and trailing rollers 46 and 48 sequentially transit over trailing edge obstacles.

Figure 8:
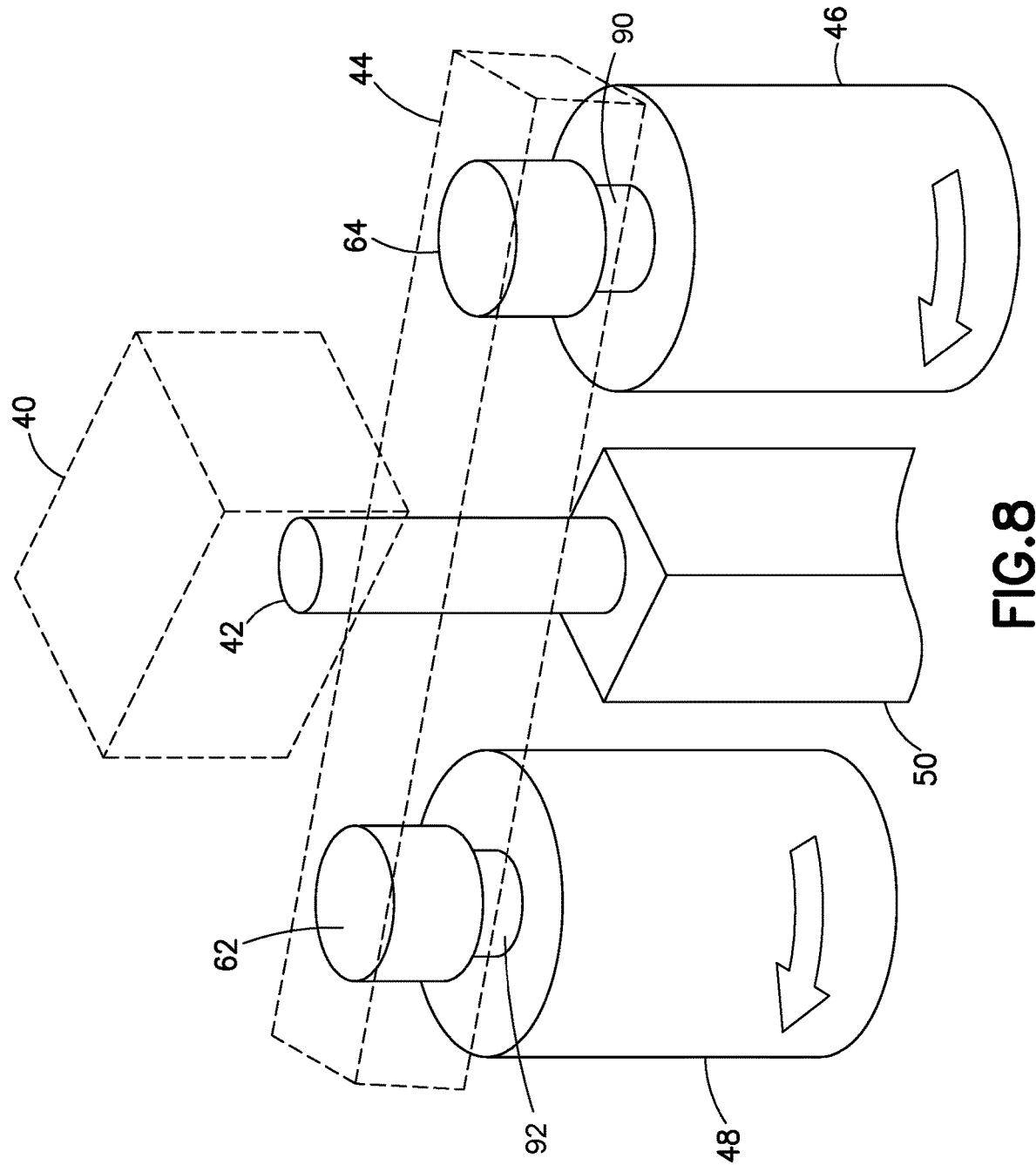

FIG. 8 is a diagram representing an isometric view of a second embodiment of the dual-roller arrangement depicted in FIGS. 6A-6C. In this embodiment, instead of the pivoting cross beam 44 being driven to rotate about axle 42 by a motor, the rollers 46 and 48 are driven to rotate (indicated by respective curved arrows) by a drive system housed inside the pivoting cross beam 44. This drive system comprises a roller drive motor 64 having an output shaft 90 connected to the leading roller 46 and a roller drive motor 62 having an output shaft 92 connected to the trailing roller 48. Accordingly, the roller drive motors 64 and 62 drive concurrent rotation of the leading and trailing rollers 46 and 48 respectively along the trailing edge of the blade. Transiting over trailing edge obstacles is accomplished by the leading and trailing rollers 46 and 48 actively driving over the contours. In accordance with this arrangement, the pivoting cross beam 44 will rotate about axle 42 in different directions as the leading and trailing rollers 46 and 48 sequentially transit over trailing edge obstacles. The roller drive motors 62 and 64 can be activated independently or they could have synchronized rotations.

Figure 9:
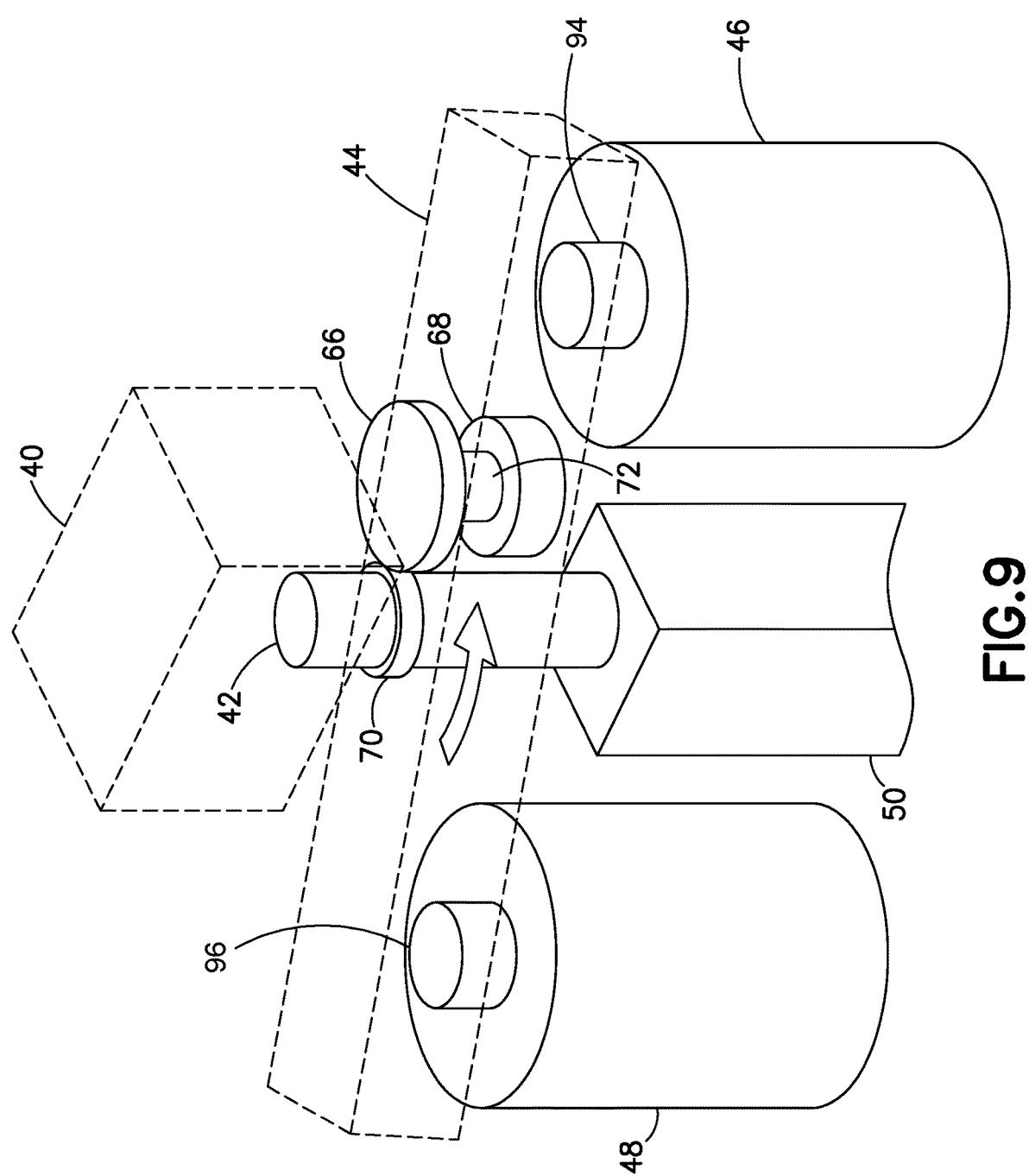

FIG. 9 is a diagram representing an isometric view of a third embodiment of the dual-roller arrangement depicted in FIGS. 6A-6C. In contrast to the embodiments depicted in FIGS. 7 and 8, in which the rollers 46 and 48 act as drive rollers, in the embodiment depicted in FIG. 9, the rollers 46 and 48 act as follower (i.e., unpowered) rollers. In this embodiment, the pivoting cross beam 44 is driven to rotate (indicated by a curved arrow) about axle 42 by a drive system partly housed inside the pivoting cross beam 44. This drive system comprises a pivot motor 68 housed inside the pivoting cross beam 44 and having an output shaft 72 connected to a pivot gear 66 disposed outside the pivoting cross beam 44. The circumference of pivot gear 66 has a multiplicity of teeth (not shown). This drive system further comprises an axle reaction gear 70 which is affixed to the axle 42 at a height outside the pivoting cross beam 44. The circumference of axle reaction gear 70 also has a multiplicity of teeth (not shown). The teeth of the pivot gear 66 engage the teeth of axle reaction gear 70 so that activation of pivot motor 68 causes the axle 42 to rotate. The leading roller 46 is rotatably coupled to an axle 94 having one end attached to one arm of the pivoting cross beam 44. Similarly, the trailing roller 48 is rotatably coupled to an axle 96 having one end attached to the other arm of the pivoting cross beam 44. Transiting over trailing edge obstacles is accomplished by the pivot motor 68 rotating the pivoting cross beam 44 to lift the rollers 46 and 48 over contours (i.e., the pivoting cross beam 44 moves the rollers 46 and 48, as previously described with reference to FIGS. 6A-6C). Some computer numeric control programming may be necessary to tell the crawler when to rotate the pivoting cross beam 44 so that the rollers 46 and 48 will transit over trailing edge obstacles. A sensor system may be employed to determine when to rotate the pivoting cross beam 44 over trailing edge obstacles (e.g., laser proximity sensor, strain sensor mounted to roller axles or to the pivoting cross beam).

Figure 10:
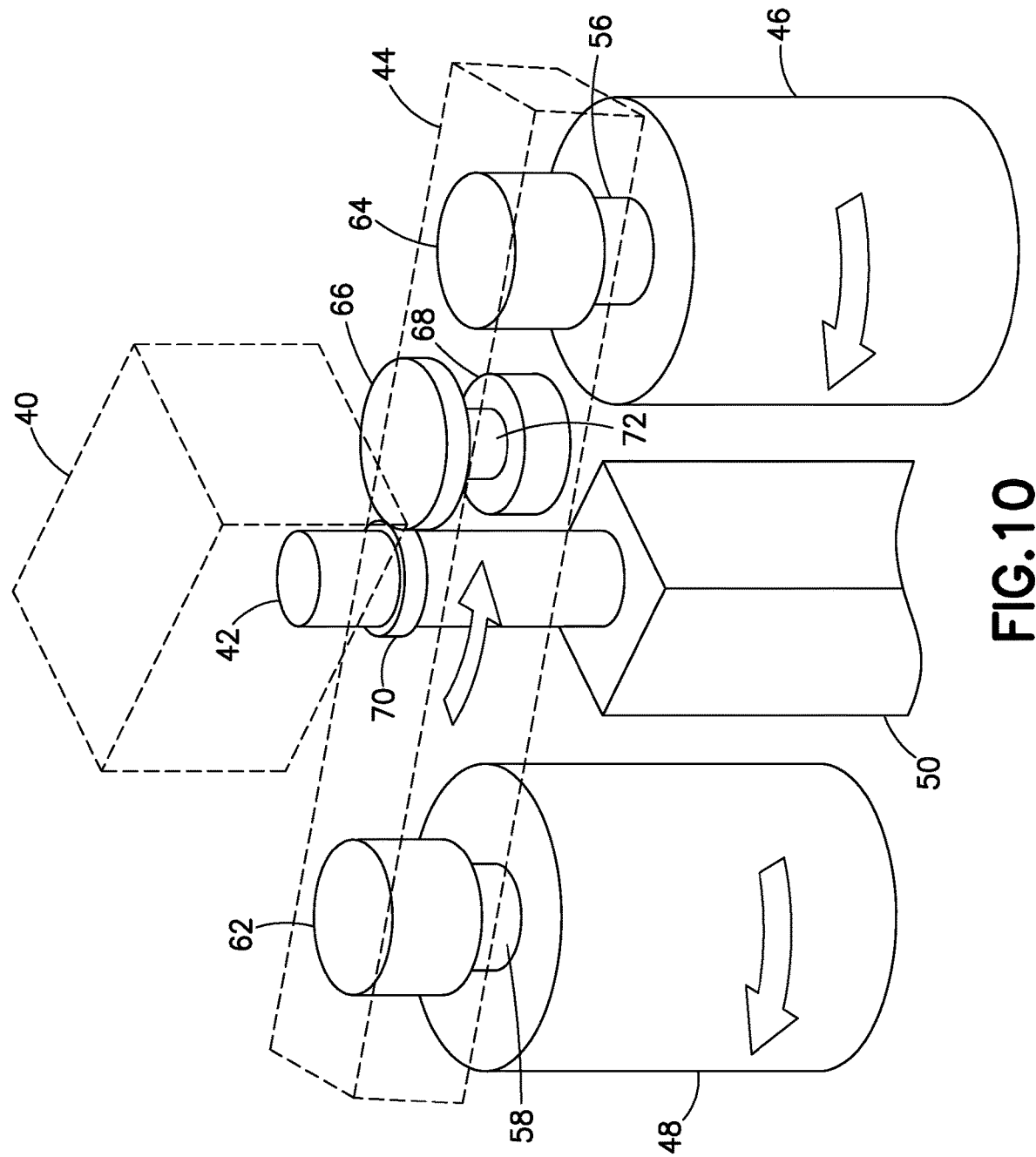

FIG. 10 is a diagram representing an isometric view of a fourth embodiment of the dual-roller arrangement depicted in FIGS. 6A-6C. This system combines the drive system for driving rotation (indicated by a curved arrow) of the pivoting cross beam 44 shown in FIG. 9 with the drive systems for driving rotation (indicated by respective curved arrows) of the rollers 46 and 48 shown in FIG. 8. Transiting over trailing edge obstacles is accomplished by both the pivot motor 68 rotating the pivoting cross beam 44 to lift the rollers 46 and 48 over contours, and the drive motors 62 and 64 actively driving the rollers 46 and 48 over the contours (i.e., the pivoting cross beam 44 and the rollers 46 and 48 move and roll in conjunction). Some computer numeric control programming may be necessary to tell the crawler when to rotate the pivoting cross beam 44 so that the rollers 46 and 48 will transit over trailing edge obstacles. A sensor system may be employed to determine when to rotate the pivoting cross beam 44 over trailing edge obstacles (e.g., laser proximity sensor, strain sensor mounted to roller axles or to the pivoting cross beam).

Figure 11:
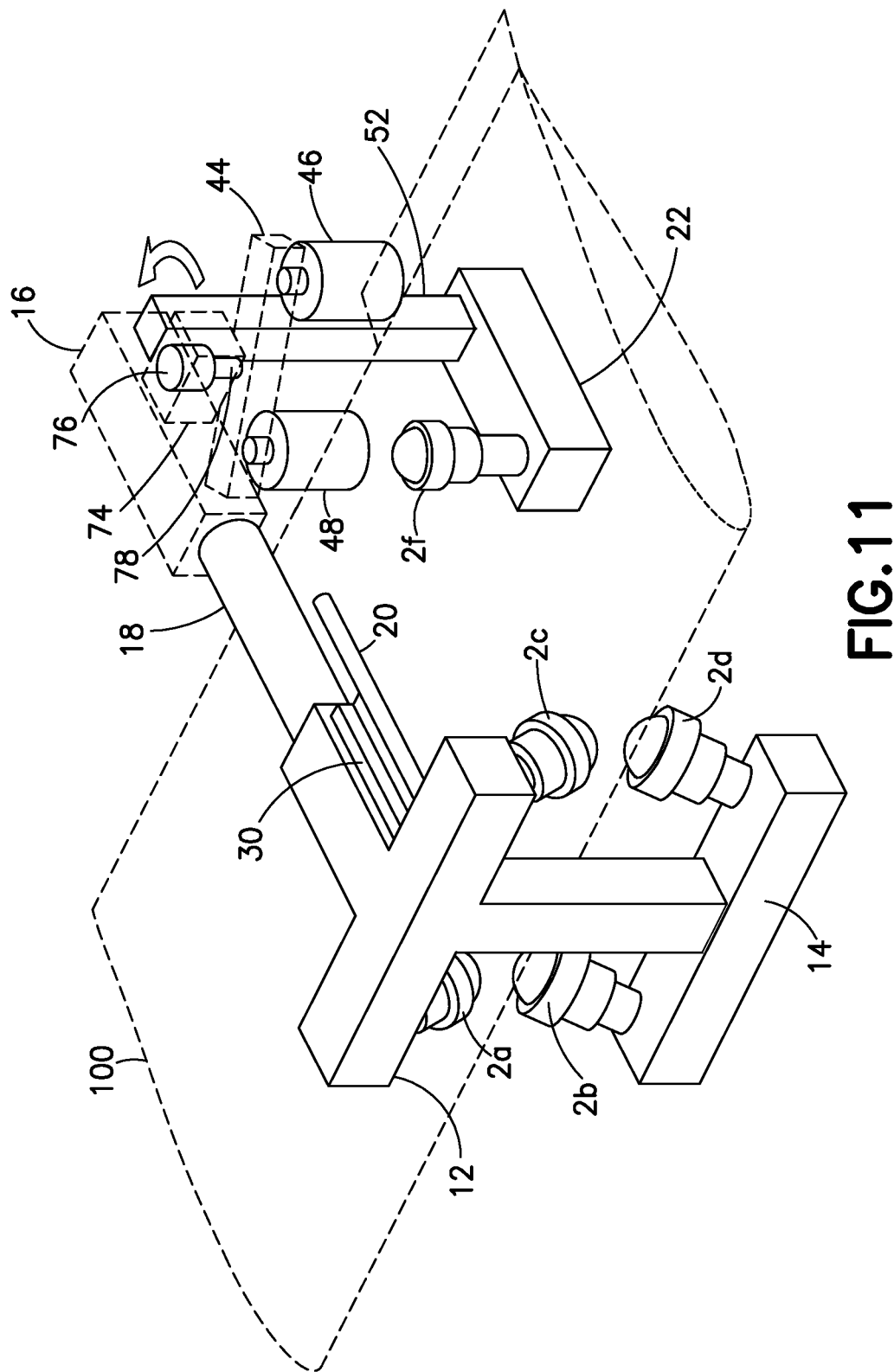
FIG. 11 is a diagram representing an isometric view of a blade crawler having a dual-roller arrangement in accordance with an alternative embodiment disposed along a trailing edge of the blade.

FIG. 11 is a diagram representing an isometric view of a blade crawler having a dual-roller arrangement in accordance with an alternative embodiment disposed along a trailing edge of the blade. In the embodiment depicted in FIG. 11, the rollers 46 and 48 act as follower (i.e., unpowered) rollers. In this embodiment, the pivoting cross beam 44 is connected to a distal end of an output shaft 78 of an axial alignment motor 76 (e.g., a stepper motor). The axial alignment motor 76 drives the pivoting cross beam 44 to rotate (indicated by a curved arrow). The axial alignment motor 76 is housed inside a motor housing 75. The motor housing 75 is attached to a generally vertical support member 52. The support member 52 has one end attached to the upper rearward body part 16 and another end attached to one end of the lower rearward body part 22 to form a strongback. The motor housing 75 is mounted to the support member 52 so that the axis of output shaft 78 is generally vertical.

Figure 12:
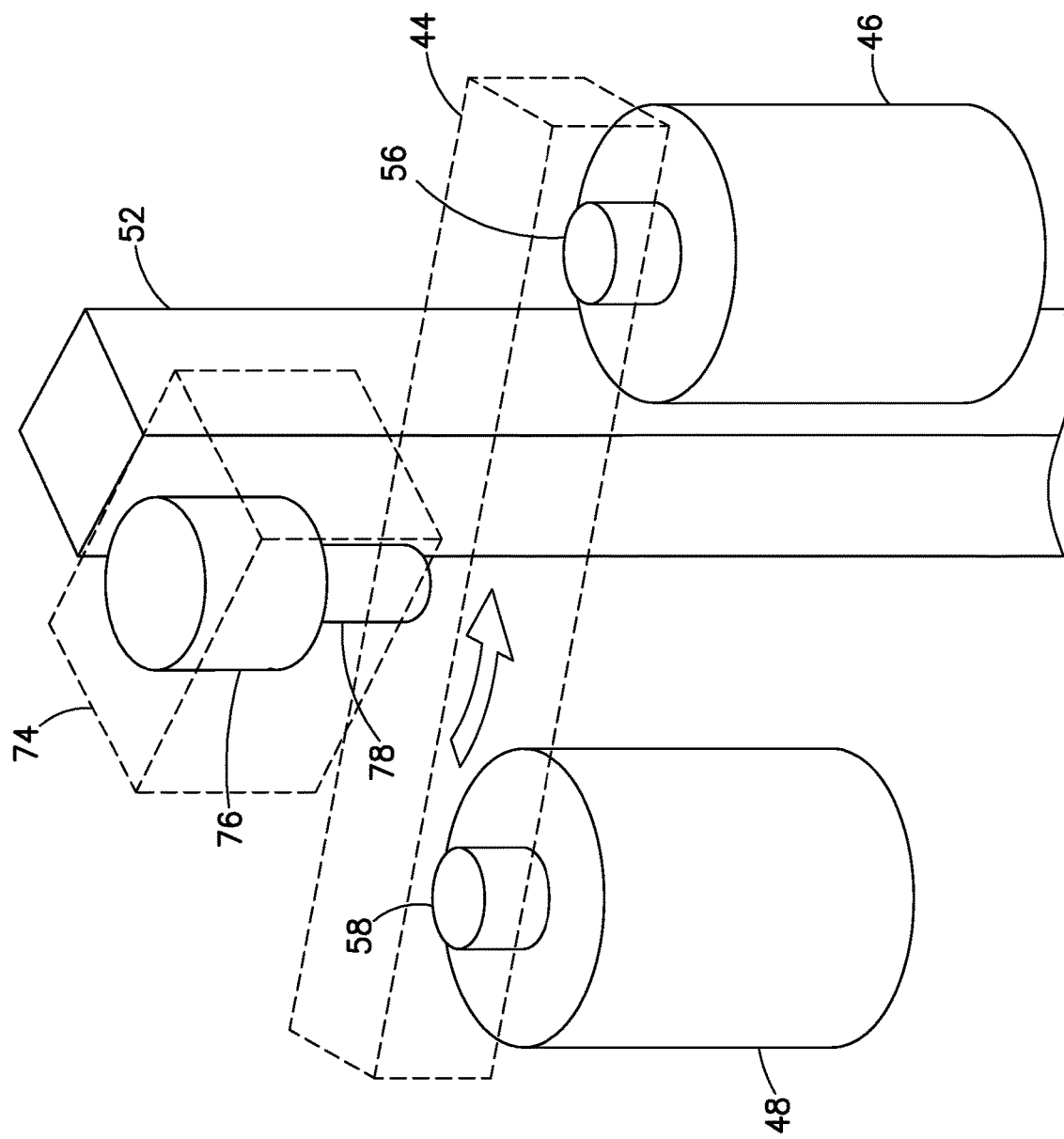
FIG. 12 is a diagram representing an isometric view on a magnified scale of the embodiment of the dual-roller arrangement depicted in FIG. 11.

FIG. 12 is a diagram representing an isometric view on a magnified scale of the embodiment of the dual-roller arrangement depicted in FIG. 11. The pivoting cross beam 44 is mounted at its midpoint to the output shaft 78. The opposing ends of the pivoting cross beam 44 support rollers 46 and 48 respectively. Preferably the axis of output shaft 78 is at the midpoint between the axes of rollers 46 and 48. When scanning a portion of the airfoil-shaped body 100 that has no trailing edge protrusions, the rearward body part 16 is positioned so that both follower rollers 46 and 48 are in contact with the trailing edge 96 of the airfoil-shaped body 100. Transiting over trailing edge obstacles is accomplished by the axial alignment motor 76 rotating the pivoting cross beam 44 to lift the rollers 46 and 48 over contours (i.e., the pivoting cross beam 44 moves the rollers 46 and 48, as previously described with reference to FIGS. 6A-6C). Some computer numeric control programming may be necessary to tell the crawler when to rotate the pivoting cross beam 44 so that the rollers 46 and 48 will transit over trailing edge obstacles. A sensor system may be employed to determine when to rotate the pivoting cross beam 44 over trailing edge obstacles (e.g., laser proximity sensor, strain sensor mounted to roller axles or to the pivoting cross beam). The crawler-aligning and protrusion-traversing devices disclosed above are not limited in their application to crawlers in which the end effector is carried by a slider that travels along a guide rod connected to a forward body part, as disclosed above. For example, a pair of mutually parallel rails may be substituted for the intercostal element and the guide rod, with the end effector being carried by a motorized carriage that travels along the dual rails. In an alternative example. A single beam may be substituted for the intercostal element and the guide rod, with the end effector being carried by a motorized device that travels along the length of the beam.

While automated blade crawlers have been described with reference to particular embodiments, it will be understood by those skilled in the art that various changes may be made and equivalents may be substituted for elements thereof without departing from the scope of the teachings herein. In addition, many modifications may be made to adapt a particular situation to the teachings herein without departing from the essential scope thereof. Therefore it is intended that the claims set forth hereinafter not be limited to the disclosed embodiments.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices comprising a processing unit (e.g., a central processing unit) and some form of memory (i.e., computer-readable medium) for storing a program which is readable by the processing unit.

The invention claimed is:

1. An automated apparatus for moving an end effector over a surface of an airfoil-shaped body, comprising:
   a chassis configured to be mounted on an airfoil-shaped body, said chassis comprising forward and rearward assemblies which are linearly displaceable relative to each other along a first axis, said rearward assembly comprising an upper rearward body part and an axle having a second axis perpendicular to said first axis and fixed relative to the upper rearward body part;

a drive roller rotatably mounted to said chassis;

a first drive motor mounted to said chassis and arranged to drive rotation of said drive roller;

a cross beam rotatably mounted to said axle of said rearward assembly of said chassis and not driven to rotate by a motor;

first and second rollers rotatably mounted to opposing ends of said cross beam for rotation about third and fourth axes respectively, said third and fourth axes being parallel to said second axis; and a second drive motor for driving rotation of said first roller about said third axis, wherein said rearward assembly further comprises a lower rearward body part and a support member having one end attached to said lower rearward body part and another end attached to one end of said axle, the apparatus further comprising a first ball and socket bearing supported by said lower rearward body part and a second ball and socket bearing supported by said upper rearward body part.

2. The apparatus as recited in claim 1, further comprising:

a drive pulley affixed to an output shaft of said second drive motor;

a first follower pulley rotatably coupled to said cross beam and fixedly coupled to said first roller; and a first drive belt or chain that couples the first follower pulley to the drive pulley.

3. The apparatus as recited in claim 2, further comprising:

a second follower pulley rotatably coupled to said cross beam and fixedly coupled to said second roller; and a second drive belt or chain that couples the second follower pulley to the drive pulley.

4. The apparatus as recited in claim 1, wherein said second axis is at a midpoint between the third and fourth axes.

5. An automated apparatus for moving an end effector over a surface of an airfoil-shaped body, comprising:

a chassis configured to be mounted on an airfoil-shaped body, said chassis comprising forward and rearward assemblies which are linearly displaceable relative to each other along a first axis, said rearward assembly comprising an upper rearward body part and an axle having a second axis perpendicular to said first axis and fixed relative to the upper rearward body part;

a drive roller rotatably mounted to said chassis;

a first drive motor mounted to said chassis and arranged to drive rotation of said drive roller;

a cross beam rotatably mounted to said axle of said rearward assembly of said chassis for rotation about the second axis perpendicular to said first axis; and first and second rollers rotatably mounted to opposing ends of said cross beam for rotation about third and fourth axes respectively, said third and fourth axes being parallel to said second axis, wherein said rearward assembly further comprises a lower rearward body part and a support member having one end attached to said lower rearward body part and another end attached to one end of said axle, the apparatus further comprising a first ball and socket bearing supported by said lower rearward body part and a second ball and socket bearing supported by said upper rearward body part.

6. The apparatus as recited in claim 5, further comprising a second drive motor arranged to drive rotation of said cross beam about said second axis.

7. The apparatus as recited in claim 6, further comprising a third drive motor arranged to drive rotation of said first roller relative to said cross beam.

8. The apparatus as recited in claim 6, wherein said rearward assembly comprises a support member, said second drive motor is mounted to said support member and comprises an output shaft, and said cross beam is mounted to said output shaft of said second drive motor.

9. The apparatus as recited in claim 6, further comprising a pivot gear mounted to an output shaft of said second drive motor and an axle reaction gear affixed to said axle, each of said pivot gear and said axle reaction gear comprising teeth that are interengaged.

10. The apparatus as recited in claim 9, wherein said second drive motor is housed inside said cross beam and said pivot gear is disposed outside said cross beam.

11. The apparatus as recited in claim 9, further comprising a third drive motor arranged to drive rotation of said first roller relative to said cross beam and a fourth drive motor arranged to drive rotation of said second roller relative to said cross beam.

12. The apparatus as recited in claim 11, wherein said second, third and fourth drive motors are housed inside said cross beam and said pivot gear is disposed outside said cross beam.

13. The apparatus as recited in claim 6, further comprising a linear actuator for linearly displacing said rearward assembly relative to said forward assembly of said chassis, said linear actuator comprising a third drive motor.

14. The apparatus as recited in claim 13, further comprising a computer system configured to control said second and third drive motors in a protrusion climbing mode such that said cross beam rotates about said second axis and linearly displaces along said first axis concurrently.

15. The apparatus as recited in claim 14, wherein said computer system is further configured to control said first drive motor in a chassis displacement mode such that said drive roller rotates while said cross beam does not rotate.

16. The apparatus as recited in claim 5, further comprising a second drive motor arranged to drive rotation of said first roller relative to said cross beam.

17. The apparatus as recited in claim 5, wherein said second axis is at a midpoint between the third and fourth axes.

* * * * *